United States Patent
Burnes et al.

(10) Patent No.: US 7,289,850 B2
(45) Date of Patent: Oct. 30, 2007

(54) SYSTEM FOR ENHANCED CARDIAC FUNCTION WITH COMBINED PESP/NES

(75) Inventors: John E. Burnes, Andover, MN (US); Lawrence J. Mulligan, Andover, MN (US); Randall L. Knoll, Stillwater, MN (US)

(73) Assignee: Medtronics, Inc., Minneapolis, MN (US)

( * ) Notice: Subject to any disclaimer, the term of this patent is extended or adjusted under 35 U.S.C. 154(b) by 219 days.

(21) Appl. No.: 11/116,941

(22) Filed: Apr. 28, 2005

(65) Prior Publication Data

US 2006/0247699 A1    Nov. 2, 2006

(51) Int. Cl.
*A61N 1/36* (2006.01)
(52) U.S. Cl. .......................................... 607/9
(58) Field of Classification Search ............... 607/9
See application file for complete search history.

(56) References Cited

U.S. PATENT DOCUMENTS 7,130,684 B2 * 10/2006 Mulligan et al. .............. 607/9
2004/0049235 A1 * 3/2004 Deno et al. .................... 607/9
2005/0090871 A1 * 4/2005 Cho et al. ..................... 607/17

* cited by examiner

*Primary Examiner*—Carl Layno
*Assistant Examiner*—Yun Haeng Lee
(74) *Attorney, Agent, or Firm*—Paul H. McDowell; Steve Bauer

(57) ABSTRACT

In some embodiments, a method of applying stimulation pulse therapy to excitable tissue may include one or more of the following steps: (a) delivering a PESP stimulation therapy to the excitable tissue for a cardiac cycle, (b) delivering a NES stimulation therapy to the excitable tissue during certain cardiac cycles, (c) determining physiologic demand of the patient based on at least one physiologic measurement, (d) determining physiologic demand being placed on a heart based on at least one physiologic measurement, and ceasing the delivery of the NES and PESP stimulation therapy when physiologic demand returns to a base level, and (e) determining physiologic demand being placed on a heart based on at least one physiologic measurement, and modulating the ratio of the number of cardiac cycles in which the NES stimulation therapy is delivered to the number of cardiac cycles in which the PESP stimulation therapy is delivered based on physiologic demand.

6 Claims, 29 Drawing Sheets

SYSTEM FOR ENHANCED CARDIAC FUNCTION WITH COMBINED PESP/NES

FIELD

Embodiments of the invention relates generally to implantable medical devices and more specifically to monitoring and treating signs of acute or chronic cardiac mechanical dysfunction such as heart failure (HF), cardiogenic shock, pulseless electrical activity (PEA), or electromechanical dissociation (EMD), and providing appropriate therapies.

BACKGROUND

Congestive heart failure is an extremely serious affliction. Heart failure (HF) is not a specific disease, but rather a compilation of ailments and symptoms, all of which are caused by an inability of the heart to appropriately increase cardiac output during exertion. HF may be caused by chronic hypertension, ischemia, tachyarrhythmias, infarct or idiopathic cardiomyopathy. The cardiac diseases associated with symptoms of congestive heart failure include dilated cardiomyopathy, restrictive/constrictive cardiomyopathy, and hypertrophic cardiomyopathy. HF has a great impact on the quality of life; the sympathetic nervous system is placed into a state of hyperexcitablity leading to a loss of heart rate variability and rate responsive mechanisms in the heart. The ability of the heart to relax is impaired resulting in elevated filling pressures, pulmonary congestion and low exercise tolerance. These are just a few of the side effects. The classical symptoms of the disease include shortness of breath, edema, and overwhelming fatigue. As the disease progresses, the lack of cardiac output may contribute to the failure of other body organs, leading to cardiogenic shock, arrhythmias, electromechanical dissociation, and death. The disease afflicts millions of individuals globally in a given year; in the USA alone there are about 400,000 new cases, 1 million hospital admissions, and $8 billion cost of care.

The treatment of severe cardiac dysfunction and decompensated heart failure may include inotropic drug therapies such as dobutamine. Although these agents may be beneficial in specific settings, they require administration of a drug, often by intravenous route, with systemic side effects and the time-consuming involvement of skilled clinicians. Electrical stimulation therapies are attractive alternatives because implanted or external devices may administer them very shortly after dysfunction appears or worsens and because their actions may be confined to the heart.

The mechanical contraction of the heart is initiated by the spread of an electrical wavefront through the cardiac tissue. This cardiac excitation-contraction coupling is closely linked to the regulation of calcium both outside and inside the myocardial cell. Electrical depolarization of cardiac myocyte results in a small amount of calcium entry into the myocyte through the L-type calcium channels. This small calcium influx causes a calcium induced calcium release from the sarcoplasmic reticulum (SR), an internal cellular structure that stores calcium. The SR released calcium binds with the myocyte actin and myocin, leading to mechanical cell shortening (contraction). The calcium is then sequestered back into the SR, resulting in removal from the actin and myocin and relaxation of the myocyte. Electrical therapies such as post extrasystolic potentiation (PESP) and nonexcitatory electrical stimulation are thought to interact with the cardiac myocyte calcium handling by enhancing SR calcium uptake and L-type calcium influx, respectively.

Delivering stimulation during the refractory period of the cardiac cycle is a type of non-excitatory stimulation (NES). NES has been observed to cause release of catecholamines such as norepinephrine within the tissue of the heart, potentially contributing to an observed increase in increased contractility of the cardiac tissue. NES may also alter calcium influx from the intra-cellular space into the cardiac myocyte, which could increase the amount of calcium available for muscles contraction both directly and through greater SR calcium uptake and subsequent release. Whatever the mechanism, application of NES has been observed to increase pressure or flow, potentially leading to fewer symptoms of heart failure, and improved exertional capacity. NES employs one or more pulses applied shortly after a sensed depolarization or delivered pacing pulse and before the resulting ventricular contraction occurs. These NES pulses are delivered during the refractory period of the cardiac tissue such that they do not result in another mechanical contraction or electrical depolarization.

Another type of electrical stimulation can be provided during the nonrefractory period of the cardiac cycle to enhance cardiac performance. This type of paired and coupled stimulation of heart tissue results in an additional electrical depolarization and, when appropriately timed, results in post extrasystolic potentiation (PESP). The additional depolarization, coming shortly after a first depolarization, is likely not associated with a sizable mechanical contraction. The contractility of subsequent cardiac cycles is increased as described in detail in commonly assigned U.S. Pat. No. 5,213,098. One possible mechanism of PESP is thought to depend on calcium cycling within the myocytes. The early extrasystole tries to initiate calcium release from the sarcoplasmic reticulum (SR) too early and as a result does not release much calcium. However, the SR continues to take up further calcium until the next electrical depolarization, resulting in enhanced SR calcium uptake and SR release on the next depolarization, leading to a more rigorous mechanical contraction.

Another known treatment for HF patients involves using atrioventricular (AV) synchronous pacing systems, including DDD and DDDR pacing devices, cardiac resynchronization therapy (CRT) devices, and defibrillation systems, to treat certain patient groups suffering heart failure symptoms. Dual chamber pacing and defibrillation systems generally pace or sense in both the right atrium and right ventricle to synchronize contractions and contribute to ventricular filling. Cardiac resynchronization devices extend dual chamber pacing to biventricular pacing to achieve better filling and a more coordinated contraction of the left and right ventricles. These pacing therapies result in greater pulse pressure, increased dP/dt, and improved cardiac output. These pacing systems may also include atrial and ventricular defibrillators or other therapies for tachyarrhythmias. As a direct result of a tachycardia or as a sequela, cardiac function may deteriorate to the point of greatly reduced cardiac output and elevated diastolic pressure. Rapid termination of tachycardias prevents worsening of heart failure.

Prior art systems have not achieved a comprehensive therapy regimen that coordinates these mechanisms in a manner that is most effective without some degree of initiating potential arrhythmia with delivering a stimulation therapy in or around the non-refractory period to achieve PESP and/or NES. Delivery of electrical stimulation as the heart tissue is becoming non-refractory can trigger a tachyarrhythmia. This is particularly true if multiple high-amplitude pacing pulses are utilized. A second factor may be a shift in the magnitude of resulting potentiation or refractory interval due to the course of disease or medication. These may lead to unacceptable levels of potentiation performance, or loss of effect altogether. Therefore, readily obtaining the appropriate timing parameters associated with this type of therapy is essential.

The above-referenced '098 patent discloses the use of PESP in a manner that utilizes one or more sensors and signal processing circuitry to control timing parameters. For example, sensed physiologic signals are used to control the frequency or number of heart cycles between the delivery of one or more additional non-refractory pacing pulses. More specifically, a first sensor such as a ventricular or arterial blood pressure or flow sensor is employed to monitor the performance of the heart and to develop a cardiac performance index (CPI). A second sensor such as an oxygen saturation sensor positioned in the coronary sinus is employed to monitor cardiac muscle stress and develop a cardiac stress index (CSI). CPI and CSI are used to govern PESP stimulation application and timing to balance performance and stress. The disclosed PESP stimulator may be incorporated into a dual chamber pacing system with or without physiologic rate control (e.g., DDD).

Another problem associated with PESP is that the added ventricular depolarization may cause the loss of AV conduction during the next cardiac cycle. This results in loss of the next intrinsic depolarization in the ventricle. Generally, this will occur during every-other cardiac cycle. This is commonly referred to as 2:1 AV block. The resulting pattern may be unstable, characterized by intermittent shifts between 2:1 and 1:1 conduction which may offset the other benefits provided by the PESP since ventricular filling is compromised.

What is needed is a system and method that combines the known therapies available for treating cardiac dysfunction including HF in a manner that optimizes mechanical function or cardiac output, while also minimizing any risks associated with possibly inducing an arrhythmia.

As discussed above, PESP therapy involves providing pulses during a non-refractory period of the ventricles. The pulses are delivered such that the ventricles experience a second depolarization some 200-300 ms following an intrinsic or paced depolarization. This results in an extra systole that increases contractile function and stroke volume on subsequent contractions. The magnitude of the enhanced function is dependent on simulation timing. Shorter extra-systolic intervals (ESIs) are known to produce greater potentiation of subsequent cardiac cycles, up to the point when the refractory period is encountered and no additional potentiation results. Likewise, NES therapy involves the delivery of pacing pulses during the refractory period that do not result in a ventricular depolarization, but still result in enhanced cardiac performance.

SUMMARY

In some embodiments, a method of applying stimulation pulse therapy to excitable tissue may include one or more of the following steps: (a) delivering a PESP stimulation therapy to the excitable tissue for a cardiac cycle, (b) delivering a NES stimulation therapy to the excitable tissue during certain cardiac cycles, (c) determining physiologic demand of the patient based on at least one physiologic measurement, (d) determining physiologic demand being placed on a heart based on at least one physiologic measurement, and ceasing the delivery of the NES and PESP stimulation therapy when physiologic demand returns to a base level, and (e) determining physiologic demand being placed on a heart based on at least one physiologic measurement, and modulating the ratio of the number of cardiac cycles in which the NES stimulation therapy is delivered to the number of cardiac cycles in which the PESP stimulation therapy is delivered based on physiologic demand.

In some embodiments, a method of applying PESP and NES stimulation pulse therapy to a excitable tissue may include one or more of the following steps: (a) determining a recirculation fraction (RF) from pressure readings taken from a chamber of the heart, (b) determining a potentiation ratio (PR) from pressure readings taken from a chamber of the heart, (c) delivering a PESP stimulation therapy to the heart after the RF is determined as being low, (d) delivering a NES stimulation therapy to the excitable tissue after the PR is determined as being low, (e) terminating delivery of the NES stimulation therapy if the PR does not increase, (f) terminating delivery of the PESP stimulation therapy if the RF does not increase, and (g) increasing the frequency of delivery of the NES stimulation therapy to the chamber after the PR is determined to be decreasing.

In some embodiments, a method of applying stimulation pulse therapy to a excitable tissue may include one or more of the following steps: (a) delivering a PESP stimulation therapy to the heart, (b) delivering a NES stimulation therapy to the heart, (c) detecting the presence of a termination event, (d) terminating the delivery of the NES stimulation therapy and the PESP stimulation therapy following detection of the termination event, (e) initiating delivery of the PESP stimulation therapy and the NES stimulation therapy following detection of an initiation event, and (f) initiating delivery of the PESP stimulation therapy and the NES stimulation therapy after a predetermined amount of time following a termination event.

DRAWINGS

DESCRIPTION OF VARIOUS EMBODIMENTS

Figure 1:
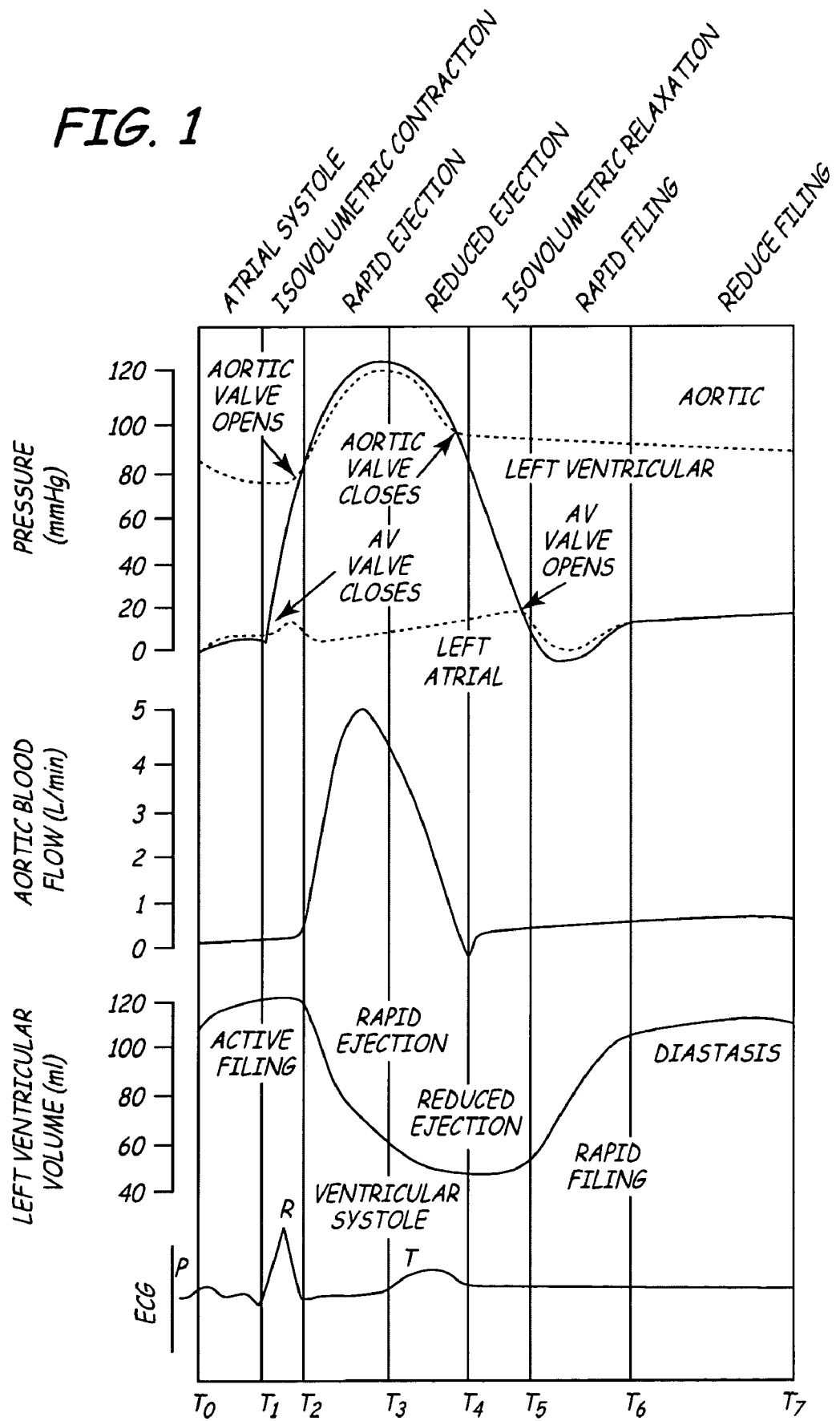
FIG. 1 depicts the relationship of heart chamber EGM, pressure, flow, and volume during a cardiac cycle.

The following discussion is presented to enable a person skilled in the art to make and use embodiments of the invention. Various modifications to the illustrated embodiments will be readily apparent to those skilled in the art, and the generic principles herein may be applied to other embodiments and applications without departing from embodiments of the invention. Thus, embodiments of the invention are not intended to be limited to embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of embodiments of the invention. Skilled artisans will recognize the examples provided herein have many useful alternatives and fall within the scope of embodiments of the invention. The following introductory material is intended to familiarize the reader with the general nature and some of the features of embodiments of the invention.

A system constructed and operated according to the embodiments of the invention that may be used to deliver the therapies discussed above may include a signal generator, timing circuit, and/or microprocessor control circuit of the type included in existing pacemaker or ICD systems as is known in the art. Exemplary systems are shown in U.S. Pat. Nos. 5,158,078, 5,318,593, 5,226,513, 5,314,448, 5,366,485, 5,713,924, 5,224,475 and 5,835,975 each of which is incorporated herein by reference, although any other type of pacing and/or ICD system may be used for this purpose. In such systems, electrogram (EGM) sensing is performed by electrodes carried on leads placed within the chambers of the heart, and/or on the housing of the device. Alternatively, subcutaneous (SQ) and/or external pad or patch electrodes may be used to sense cardiac signals. Physiologic sensors may likewise be carried on device housings lead or SQ systems according to any of the configurations and/or sensing systems known in the art.

All embodiments of the invention disclosure electrode configurations to deliver electrical stimulation energy where necessary and to time the delivery of this energy to achieve beneficial effects while avoiding unsafe delivery (as further described herein below). For each therapy component described above, specific electrode locations and geometries may be preferred. The locations for the electrodes of these embodiments of the invention for stimulation include: use of large surface area defibrillation coil electrodes in the heart or adjacent to the heart; pacing electrodes at locations including RV apex, outflow tract, atrial locations, HIS bundle site, left side epicardium, pericardial surface of the heart or endocardium; sympathetic nerve regions near the cervical or thoracic spine or nerves or adjacent vessels on or near the heart; transthoracic electrodes including paddles and patches, can electrode, temporary electrodes (e.g., epicardial, transvenous or post-operative electrodes), subcutaneous electrodes, linked microelectrode arrays, and multiple site stimulation.

In accordance with common biomedical engineering practices, stimulation therapy is applied with minimized net charge delivery to reduce corrosion and counteract polarization energy losses. Both energy efficient therapy delivery and electrogram (EGM) sensing benefit from low polarization lead systems. Finally, the electrodes are preferably connected to fast recovery amplifiers that allow EGM sensing soon after therapy delivery.

The most fundamental sensors are those based on electrograms (ECG or EGMs) and reflect cardiac electrical activity. These sensors require electrodes located where they can readily detect depolarization and repolarization signals as well as sense amplifiers for the monitoring of heart rhythm and diagnosis of arrhythmias.

According to one embodiment, blood pressure sensors, accelerometers, flow probes, microphones, or sonometric crystals may be used to measure flow, force, velocity, movement of the walls of the heart, and/or to estimate the volume of the cardiac chambers. Parameters derived from these sensors can also be used to detect the onset and severity of cardiac hemodynamic dysfunction. For example, HF decompensation may be indicated when a change in long-term left ventricle diastolic pressure has increased while contractility of the heart derived from dP/dt rate of rise of ventricular pressure ($dP/dt_{max}$) has diminished. Although pressure sensors figure prominently in the examples above a number of other sensors could reflect mechanical function.

Intracardiac or transthoracic impedance changes reflect mechanical function, stroke volume, and cardiac output. Accelerometers or microphones within the body or applied externally sense cardiac dysfunction and monitor the response to therapy. Heart volume, dimension changes, and velocities may be measured by implanted or external applications of ultrasound. Implantable oxygen sensors may also measure the extent of vascular perfusion as an indicator of heart function.

Another embodiment of embodiments of the invention may utilize changes in transthoracic or intracardiac impedance signals to sense cardiac motion and respiratory movement. Changes in intra-thoracic impedance as a result of pulmonary edema may also be used to trigger PESP and/or NES stimulation therapy.

In implantable or external devices, metabolic or chemical sensors such as expired $CO_2$ and blood oxygen saturation, pH, $pO_2$, and/or lactate) may be employed to reflect cardiac dysfunction and used to trigger the appropriate stimulation therapy.

Non-excitatory stimulation (NES) is generally a sub-threshold stimulation applied to cardiac tissue during the refractory period. This form of NES is thought to affect ion permeabilities across the myocyte membrane through direct electrical influence on the myocyte ion channels or through indirect mechanisms related to the release of neurohormonal modulators such as catecholamine acting on the myocytes. According to another aspect of embodiments of the invention, another type of non-excitatory stimulation is nonexcitatory electrical neurostimulation therapies that are directed at sympathetic nerves in the neck, chest, mediastinum, and heart to enhance mechanical function through neurohormonal modulation. These therapies are known as nonexcitatory electrical stimulation (NES) therapies because they are not intended to cause cardiac tissue depolarization and can be accomplished with electrode locations and/or stimulation timing that avoid electrically exciting cardiac tissue. Electrodes near the heart deliver one or more NES pulses within the refractory period of the myocardium. Of course, electrodes that are not in proximity to the heart or those that are, but direct electrical current away from the myocardium may deliver electrical stimuli at various times throughout the cardiac cycle without directly exciting cardiac tissue.

Another aspect of embodiments of the invention involves delivering electrical stimulation to the atrium and ventricles in a manner that optimizes resulting mechanical function including pressures and flows while minimizing associated potential induction of arrhythmia. Several features of embodiments of the invention are provided to achieve this goal, including regulation of both NES and PESP therapy delivery to attain the desired level of enhanced function and a delivery rule to inhibit or lockout PESP therapy when it is at risk of being proarrhythmic, diminishing diastole and coronary blood flow, and/or reducing the beneficial effect on hemodynamics. Rapid PESP therapy heart rates are a prime example of when PESP therapy may be counter productive and thus may necessitate the use of such delivery lockout rules.

A delivery lockout rule operates on a short term or beat-by-beat basis to disable PESP if the V-V interval from the prior cycle is too short. Thus, ectopy will suppress PESP therapy as, for example, will sinus tachycardia, other SVTs, VTs, and VF. The inventors have discovered that this rule is a key component of safe and effective PESP stimulation therapy in a variety of situations.

The application of PESP and NES therapy according to embodiments of the invention may be altered by (i) a physician (based on laboratory results and the patient's signs and symptoms), (ii) by the patient (to help with anticipated or present symptoms such as associated with exertion), or (iii) automatically by device sensors that detect conditions of enhanced physiologic demand or cardiovascular compromise that may be responsive to these stimulation therapies. In each of these cases there may be distinct maximal therapy durations and termination criteria (or therapy may be ended by the physician or patient).

Automated sensor-governed initiation of stimulation therapies are described herein. If there is no current arrhythmia, physiologic sensors may be employed to determine if cardiac hemodynamic dysfunction driven therapy is to be initiated. Blood pressure signals such as arterial, right ventricular, and/or left ventricular pressure sensors (which may be utilized to derive other discrete cardiovascular pressure measurements) may be used to obtain respective pressure measurements. Therapy may be initiated when these measurements indicate a pressure change that drops below or exceeds a predetermined threshold for an established period of time. In one example depicted in detail herein, a severe level of dysfunction (LV dP/dt max<400 mmHg/s) is observed during normal sinus rhythm for over six seconds. The pressure measurements may be weighted and/or combined to obtain a statistic used to trigger therapy delivery. The statistic may be used to develop long-term trend data used to indicate the onset and severity of HF and hemodynamic dysfunction as well as monitor effectiveness of therapy.

In another aspect of embodiments of the invention, RV pressure is used to derive RV end-diastolic and developed pressure, maximum pressure change as a function of time (dP/dtmax), an estimate of pulmonary artery diastolic pressure (ePAD), an RV relaxation time constant (tau), or RV recirculation fraction (RF). These derived parameters are then used to determine when the degree of dysfunction has exceeded an acceptable level such that therapy delivery is initiated. Parameters could be measured or computed as above and compared to thresholds, or sensor signals could be processed and cardiac dysfunction identified through template matching and classification. Thresholds and/or classification schemes may be periodically updated to reject any natural changes in the condition of the patient as cause for therapy.

Embodiments of the invention may also incorporate predicted hemodynamic compromise through an extended analysis of cardiac cycle-length. For example, a long duration and rapid SVT, VT, or VF has a high likelihood of producing dysfunction including acute HF decompensation, cardiogenic shock, or even electromechanical dissociation (EMD) or pulseless electrical activity (PEA) after spontaneous termination or cardioversion. In such cases, a trial of stimulation therapy might be programmed without mechanical, metabolic, or chemical sensor confirmation.

Other signals such as surface electrocardiogram (ECG) or electrogram (EGM) signals from electrodes within the patient's body may be used to detect dysfunction and heart failure (HF). For example, the ST segment level of a cardiac cycle (PQRST) detected by an ECG may be monitored. An elevated or depressed ST segment level has been found to be reliable indicator of ischemia, a condition known to be associated with dysfunction and HF. Alternatively, the duration of the Q-T interval may also be used to detect hemodynamic dysfunction. For example, a shortened Q-T interval may indicate myocardial dysfunction. A template-matching algorithm such as a wavelet classification algorithm may be used to identify electrogram signals that are associated with hemodynamic dysfunction.

Chemical sensors may be used to initiate therapy, including sensors that analyze the blood to detect changes in lactate, $O_2$ saturation, $PO_2$, $PCO_2$ and pH. Expired gas may be analyzed for $PCO_2$ as an indicator of cardiac output during resuscitation procedures. Therapy is then continued until the degree of dysfunction or HF reflected by these variables is less than a predetermined amount for a sufficient period of time.

Although pressure sensors figure prominently in the examples above a number of other sensors could reflect mechanical function. Intracardiac or transthoracic impedance changes reflect mechanical function, stroke volume, and cardiac output. Accelerometers or microphones within the body or applied externally sense serious cardiac dysfunction and monitor the response to therapy. Heart volume, dimension changes, and velocities may be measured by implanted or external applications of ultrasound.

Physiologic signals may continue to be sensed to determine if a therapy termination condition is met so that therapy may be terminated. The use, however, of a mechanical sensor such as a pressure sensor or an accelerometer to determine whether or not to apply therapy has the drawback in that external treatments of PEA/EMD such as cardiac chest compressions may introduce error into the physiologic signals, inhibiting or delaying therapy when it may be needed. An additional aspect of embodiments of the invention is to include not only a mechanical sensor in or on the heart to detect cardiac function, but a second sensor or a multitude of sensors away from the heart, such as inside the implantable device housing or can (acting as an indifferent electrode). From this second sensor, CPR artifact (due to chest compressions and the like) could be identified and, for example, subtracted to reveal a more accurate assessment of true cardiac function.

Therapy is ordinarily automatically interrupted on detection of an arrhythmic event. Upon termination of the arrhythmic event, the therapy may be automatically reconfigured to reduce risk of re-induction. Therapy could also be interrupted on detection of a sufficient quantity of abnormal depolarizations such as premature ventricular contractions (PVC). One or more PVCs could be detected through the use of rate limits or through a template matching type algorithm such as a wavelet classification algorithm, or using a PR-logic® type rhythm discrimination scheme which is a proprietary detection technique of Medtronic, Inc.

Although beneficial for cardiac function, the delivery of PESP stimulation pulses must be controlled so as to minimize the risk of inducing an arrhythmia. This is best realized with reference to the traces of an ECG or EGM signal aligned with a stimulus-intensity curve to show the intensity of pulses required to induce an extra systole during the time period following a ventricular depolarization which coincides to the QRS complex at an initial time zero (0). During the absolute refractory period, the ventricles are refractory so that another depolarization will not be induced by delivery of electrical stimulation. Following this time, the tissue recovers so that another electrical depolarization is possible upon the delivery of electrical stimulation to the cardiac tissue. The amount of electrical current required to cause the extra systole during this time is represented by the stimulus-intensity curve.

Initially, after the refractory period, the electrical current level required to capture the tissue is high but thereafter sharply decreases to a baseline level of roughly 0.5-1 mA for an implanted pacing lead.

Also, the "vulnerable period" of the ventricles must be considered when administering NES and PESP therapy. The vulnerable period represents a time period during which an electrical pulse delivered at, or above, a pre-determined amplitude has the risk of inducing a VT or VF episode. For example, a pulse delivered at about 170 ms having an amplitude of 40 mA or more may induce an tachyarrhythmia.

The importance of identifying and techniques for identifying the refractory-nonrefractory boundary is described herein. Nonexcitatory stimulation benefits arise from pulses applied anywhere in the refractory period. Stimulation delivered outside the refractory period is frequently excitatory (and will be addressed in the excitatory PESP analysis which follows herein below).

The level of enhancement or potentiation resulting from excitatory PESP stimulation therapy follows a potentiation response curve as further described herein. The inventors have found that such electrical stimulation pulses delivered shortly after the refractory period ends produce strong subsequent contractions. Further delays of the stimulation diminish the amount of potentiation. Stimulation too early (i.e., prematurely) results in no additional potentiation at all since the myocardium is refractory. As discussed with respect to the vulnerable period, the risk of arrhythmia induction is confined to a relatively narrow time interval just slightly longer than the refractory period. However, the inventors have discovered that such a risk is quite low if single low amplitude PESP pulses are delivered according to delivery lockout rules (such as briefly described above). A composite benefit function for PESP stimulation therapy is disclosed and illustrated herein. The low amplitude PESP pulse is essentially "benefit neutral" when restricted to the absolute refractory period, is not without risk for a short period just slightly longer then the refractory period, rises to a maximum benefit shortly after this short period, and finally declines to again become approximately "benefit neutral" for pulses delivered near the intrinsic cycle length.

As a result, it is apparent that stimulation timing with respect to the refractory-nonrefractory period boundary is a critical aspect of obtaining the desired response (NES or PESP) and controlling risks and benefits of therapy delivery. Embodiments of the invention provides for means to determine this time from electrical, and/or mechanical sensor signals and thereby enable safer and more effective stimulation therapies.

The inventors exploit the fact that the refractory period is closely associated with the Q-T interval, which may be derived from electrogram signals or other physiologic sensor signals by techniques known in the art. The Q-T interval length is used to estimate the duration of the refractory period either directly, or by incorporating a function of heart rate and sensing delays. In the case of PESP therapy, the Q-T interval length can be estimated by the time interval from an extra systole stimulation pulse to an evoked T wave and would be slightly longer than during a cardiac cycle not associated with PESP. This is because the extra depolarization caused by the PESP prolongs the QT interval slightly.

Alternatively, an evoked response of the PESP stimulation could be monitored to indicate whether the PESP therapy was delivered in the refractory period or not. For example, a number of electrical pulses are applied to the myocardium, beginning during the refractory period. The result of each pulse is sensed on an EGM from either the stimulating electrode or an auxiliary electrode until an evoked response is sensed, indicating that the pulse caused an extra systole. At this point, no further pulses would be applied to minimize the risk of inducing arrhythmias.

In another example, a single pulse's amplitude and timing may be manipulated until capture is detected by an evoked R wave. If capture is lost, the stimulus pulse is delayed more, or amplitude increased, or the number of pulses in a PESP pulse train is increased. Also, the characteristics of a pressure waveform (or any other mechanical response variable) used to assess whether the PESP stimulation is/was capturing the ventricles can be utilized when practicing embodiments of the invention. The presence of the extra systole could be identified by a small ventricular pressure pulse 5-80% of the size of the preceding pressure pulse or through a suitable algorithm such as a template-matching algorithm. A transition between capture and noncapture for a pulse intended to serve as an extrasystole may also be identified by a change in the pressure waveform of the subsequent potentiated beat. This can be clearly illustrated with respect to the arterial pulse pressure.

The inventive system may also deliver optional NES using a waveform including one or more pulses during the refractory period. To ensure that the NES stimulation does not enter the vulnerable period, the length of the refractory period is estimated using the mechanisms discussed above. If NES is exclusively intended, then detection of an extra systole should result in a reduction of the stimulus delay time, amplitude, or pulse number.

As the refractory-nonrefractory boundary is very important and varies from patient to patient and even with a patient over time, with disease and drugs, these methods are to be employed periodically or continually to the stimulation timing algorithm portion of the device. If this boundary information is not used to set pulse timing directly, it may be employed to establish limits for the timing that is in turn set by a clinician or some automatic control algorithm such as that described next.

A representative heart and cardiovascular system is influenced by electrical therapies including pacing, defibrillation, CRT, PESP and, NES stimulation therapy. Electrical, mechanical, and metabolic/chemical sensors may monitor the heart and cardiovascular system. The signals from these sensors influence decisions to start or stop therapy, refractory period detection, and therapy delivery lockout rules.

Before describing embodiments of the invention, reference is made to FIG. 1 which depicts the electrical depolarization waves attendant a normal sinus rhythm cardiac cycle in relation to the fluctuations in absolute blood pressure, aortic blood flow and ventricular volume in the left heart. The right atria and ventricles exhibit roughly similar pressure, flow, and volume fluctuations, in relation to the PQRST complex, as the left atria and ventricles. It is understood that the monitoring and stimulation therapy aspects of these teachings may reside and act on either or both sides of the heart. The cardiac cycle is completed in the interval between successive PQRST complexes and following relaxation of the atria and ventricles as the right and left atria re-fill with venous and oxygenated blood. In sinus rhythm, the interval between depolarizations may be on the order of 500 ms to 1,000 ms for a corresponding sinus heart rate of 120 bpm to 60 bpm, respectively. In this time interval, the atria and ventricles are relaxed, and overall atrial size or volume may vary as a function of pleural pressure and respiration. In the blood pressure diagrams of FIG. 1, it may be observed that the atrial and ventricular blood pressure changes track and lag the P-waves and R-waves of the cardiac cycle. The time period $T_0$-$T_1$ encompasses the AV interval.

In patients suffering from cardiac output insufficiency arising from bradycardia due to an incompetent SA node or AV-block, atrial and/or ventricular conventional pacing may be prescribed to restore a sufficient heart rate and AV synchrony. In FIG. 1, for example, atrial and/or ventricular pacing pulses would precede the P-wave and the deflection of the QRS complex commonly referred to as the R-wave. Cardiac output may be reduced by the inability of the atrial or ventricular myocardial cells to relax following atrial ($T_0$-$T_1$) and ventricular ($T_1$-$T_4$) systolic periods. Prolonged systolic time periods reduce passive filling time $T_4$-$T_7$ as shown in FIG. 1. Thus, the amount of blood expelled from the atria and/or ventricles in the next cardiac cycle may be less than optimum. This is particularly the case with CHF (Congestive Heart Failure) patients or other patients in whom the stiffness of the heart is increased, cardiac filling during the passive filling phase ($T_4$-$T_7$) and during atrial systole ($T_0$-$T_1$) can be significantly limited.

It will be appreciated from the following description that the implantable medical device (IMD) of embodiments of the invention may be utilized to obtain the aforementioned parameters as stored patient data over a period of time and to deliver therapies for treating the heart failure. The physician is able to initiate uplink telemetry of the patient data in order to review it to make an assessment of the heart failure state of the patient's heart. The physician can then determine whether a particular therapy is appropriate, prescribe the therapy for a period of time while again accumulating the stored patient data for a later review and assessment to determine whether the applied therapy is beneficial or not, thereby enabling periodic changes in therapy, if appropriate. Such therapies include drug therapies and electrical stimulation therapies, including PESP and/or NES stimulation, and pacing therapies including single chamber, dual chamber and multi-chamber (bi-atrial and/or bi-ventricular) pacing. Moreover, in patients prone to malignant tachyarrhythmias, the assessment of heart failure state can be taken into account in setting parameters of detection or classification of tachyarrhythmias and the therapies that are delivered.

Accordingly, an embodiment of the invention is disclosed in detail in the context of a multi-chamber pacing system that is modified to derive the aforementioned parameters indicative of cardiac mechanical dysfunction from sensors, sense electrodes and electrical stimulation electrodes located in operative relation to one or more heart chambers. This embodiment of embodiments of the invention may be programmed to operate as an AV sequential, bi-atrial , or bi-ventricular pacing system operating in demand, atrial tracking, and triggered pacing for restoring synchrony in depolarizations and contraction of left and right ventricles in synchronization with atrial sensed and paced events for treating HF and/or bradycardia. This embodiment of embodiments of the invention is therefore programmable to operate as a two, three or four channel pacing system having an AV synchronous operating mode for restoring upper and lower heart chamber synchronization and right and left atrial and/or ventricular chamber depolarization synchrony. However, it will be understood that only certain of the components of the complex multi-chamber pacing system described below can be selectively programmed to function as or be physically incorporated into a simpler, single chamber, monitoring/stimulation system for deriving the parameters indicative of heart failure state and delivering a sub-set of the aforementioned therapies.

Figure 2:
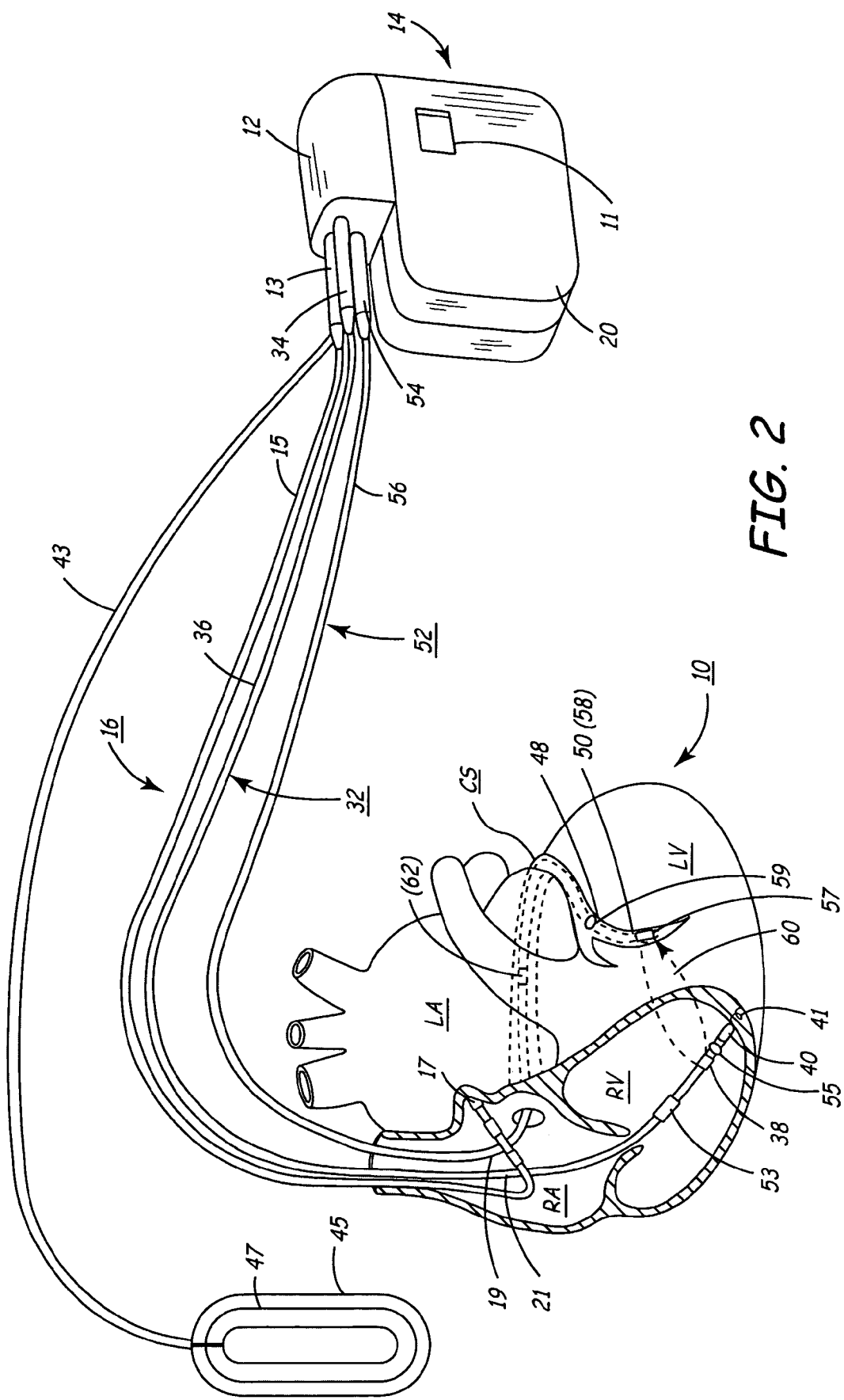
FIG. 2 is a schematic diagram depicting a multi-channel, atrial and bi-ventricular, monitoring/pacing IMD in which embodiments of the invention is preferably implemented.

In FIG. 2, heart 10 includes the upper heart chambers, the right atrium (RA) and left atrium (LA), and the lower heart chambers, the right ventricle (RV) and left ventricle (LV) and the coronary sinus (CS) extending from the opening in the right atrium laterally around the atria to form the great vein that extends further inferiorly into branches of the great vein. The cardiac cycle commences normally with the generation of the depolarization impulse at the SA Node in the right atrial wall. The impulse then conducts through the right atrium by way of internodal tracts, and conducts to the left atrial septum by way of Bachmann's bundle. The RA depolarization wave reaches the atrio-ventricular (AV) node and the atrial septum within about 40 msec and reaches the furthest walls of the RA and LA within about 70 msec. Approximately 50 ms following electrical activation, the atria contract. The aggregate RA and LA depolarization wave appears as the P-wave of the PQRST complex when sensed across external ECG electrodes and displayed. The component of the atrial depolarization wave passing between a pair of unipolar or bipolar pace/sense electrodes, respectively, located on or adjacent the RA or LA is also referred to as a sensed P-wave. Although the location and spacing of the external ECG electrodes or implanted unipolar atrial pace/sense electrodes has some influence, the normal P-wave width does not exceed 80 msec in width as measured by a high impedance sense amplifier coupled with such electrodes. A normal near field P-wave sensed between closely spaced bipolar pace/sense electrodes and located in or adjacent the RA or the LA has a width of no more than 60 msec as measured by a high impedance sense amplifier.

The depolarization impulse that reaches the AV Node conducts down the bundle of His in the intraventricular septum after a delay of about 120 msec. The depolarization wave reaches the apical region of the heart about 20 msec later and then travels superiorly though the Purkinje Fiber network over the remaining 40 msec. The aggregate RV and LV depolarization wave and the subsequent T-wave accompanying re-polarization of the depolarized myocardium are referred to as the QRST portion of the PQRST cardiac cycle complex when sensed across external ECG electrodes and displayed. When the amplitude of the QRS ventricular depolarization wave passing by a bipolar or unipolar pace/sense electrode pair located on or adjacent to the myocardium exceeds a threshold amplitude, it is detected as a sensed R-wave. Although the location and spacing of the external ECG electrodes or implanted unipolar ventricular pace/sense electrodes has some influence on R-wave sensing, the normal R-wave duration does not exceed 80 msec as measured by a high impedance sense amplifier. A normal near field R-wave sensed between closely spaced bipolar pace/sense electrodes and located in or adjacent the RV or the LV has a width of no more than 60 msec as measured by a high impedance sense amplifier.

The normal electrical activation sequence becomes highly disrupted in patients suffering from advanced HF and exhibiting intra-atrial conduction delay (IACD), left bundle branch block (LBBB), right bundle branch block (RBBB), and/or intraventricular conduction delay (IVCD). These conduction defects give rise to dyssynchrony between RV and LV activation. In RBBB and LBBB patients, the QRS complex is widened beyond the normal range to between 120 msec and 250 msec as measured on surface ECG. This increased width demonstrates the lack of synchrony of the right and left ventricular depolarizations which is often linked to dyssynchronous contractions.

FIG. 2 also depicts an implanted, multi-channel cardiac pacemaker, ICD, IPG (implantable pulse generator) or other IMD of the above noted types for restoring AV synchronous contractions of the atrial and ventricular chambers and simultaneous or sequential pacing of the right and left ventricles. The pacemaker IPG 14 is implanted subcutaneously in a patient's body between the skin and the ribs. Three endocardial leads 16, 32, and 52 connect the IPG 14 with the RA, the RV and the LV, respectively. Each lead has at least one electrical conductor and pace/sense electrode, and a remote indifferent can electrode 20 is formed as part of the outer surface of the housing of the IPG 14. As described further below, the pace/sense electrodes and the remote indifferent can electrode 20 (IND_CAN electrode) can be selectively employed to provide a number of unipolar and bipolar pace/sense electrode combinations for pacing and sensing functions. The depicted positions in or about the right and left heart chambers are also merely exemplary. Moreover other leads and pace/sense electrodes may be used instead of the depicted leads and pace/sense electrodes that are adapted to be placed at electrode sites on or in or relative to the RA, LA, RV and LV.

The depicted bipolar endocardial RA lead 16 is passed through a vein into the RA chamber of the heart 10, and the distal end of the RA lead 16 is attached to the RA wall by an attachment mechanism 17. The bipolar endocardial RA lead 16 is formed with an in-line connector 13 fitting into a bipolar bore of IPG connector block 12 that is coupled to a pair of electrically insulated conductors within lead body 15 and connected with distal tip RA pace/sense electrode 19 and proximal ring RA pace/sense electrode 21. Delivery of atrial pace pulses and sensing of atrial sense events is effected between the distal tip RA pace/sense electrode 19 and proximal ring RA pace/sense electrode 21, wherein the proximal ring RA pace/sense electrode 21 functions as an indifferent electrode (IND_RA). Alternatively, a unipolar endocardial RA lead could be substituted for the depicted bipolar endocardial RA lead 16 and be employed with the IND_CAN electrode 20. Or, one of the distal tip RA pace/sense electrode 19 and proximal ring RA pace/sense electrode 21 can be employed with the IND_CAN electrode 20 for unipolar pacing and/or sensing.

Bipolar, endocardial RV lead 32 is passed through the vein and the RA chamber of the heart 10 and into the RV where its distal ring and tip RV pace/sense electrodes 38 and 40 are fixed in place in the apex by a conventional distal attachment mechanism 41. The RV lead 32 is formed with an in-line connector 34 fitting into a bipolar bore of IPG connector block 12 that is coupled to a pair of electrically insulated conductors within lead body 36 and connected with distal tip RV pace/sense electrode 40 and proximal ring RV pace/sense electrode 38, wherein the proximal ring RV pace/sense electrode 38 functions as an indifferent electrode (IND_RV). Alternatively, a unipolar endocardial RV lead could be substituted for the depicted bipolar endocardial RV lead 32 and be employed with the IND_CAN electrode 20. Or, one of the distal tip RV pace/sense electrode 40 and proximal ring RV pace/sense electrode 38 can be employed with the IND_CAN electrode 20 for unipolar pacing and/or sensing.

In this illustrated embodiment, a unipolar, endocardial LV CS lead 52 is passed through a vein and the RA chamber of the heart 10, into the CS and then inferiority in a branching vessel of the great vein 48 to extend the distal LV CS pace/sense electrode 50 alongside the LV chamber. The distal end of such LV CS leads is advanced through the superior vena cava, the right atrium, the ostium of the coronary sinus, the coronary sinus, and into a coronary vein descending from the coronary sinus, such as the great vein. Typically, LV CS leads and LA CS leads do not employ any fixation mechanism and instead rely on the close confinement within these vessels to maintain the pace/sense electrode or electrodes at a desired site. The LV CS lead 52 is formed with a small diameter single conductor lead body 56 coupled at the proximal end connector 54 fitting into a bore of IPG connector block 12. A small diameter unipolar lead body 56 is selected in order to lodge the distal LV CS pace/sense electrode 50 deeply in a vein branching inferiority from the great vein 48.

Preferably, the distal, LV CS active pace/sense electrode 50 is paired with the proximal RV defibrillation coil 53 or can 20 for delivering LV pace pulses. The distal LV CS active pace/sense electrode 50 is also preferably paired with the distal tip RV active pace/sense electrode 40 for sensing across the RV and LV as described further below.

Moreover, in a four-chamber embodiment, LV CS lead 52 could additionally bear a proximal LA CS pace/sense electrode positioned along the lead body to lie in the larger diameter coronary sinus CS adjacent the LA. In that case, the lead body 56 would encase two electrically insulated lead conductors extending proximally from the more proximal LA CS pace/sense electrode(s) and terminating in a bipolar connector 54. The LV CS lead body may also be smaller between the proximal LA CS electrode and the distal LV CS active pace/sense electrode 50. RA pacing and sensing could occur between electrode 17 and housing 20.

Typically, in pacing/defibrillation systems of the type illustrated in FIG. 2, the electrodes designated above as "pace/sense" electrodes are used for both pacing and sensing functions. In accordance with one aspect of embodiments of the invention, these "pace/sense" electrodes can be selected to be used exclusively as pace or sense electrodes or to be used in common as pace/sense electrodes in programmed combinations for sensing cardiac signals and delivering pace pulses along pacing and sensing vectors. Separate or shared indifferent pace and sense electrodes can also be designated in pacing and sensing functions. For convenience, the following description separately designates pace and sense electrode pairs where a distinction is appropriate. With respect to embodiments of the invention, a subcutaneous electrode 45 coupled to medical electrical lead 43 may be added to or substituted for one or more of the leads or electrodes depicted in FIG. 2. If a subcutaneous electrode 45 is utilized, a suitable defibrillation coil 47 may be coupled to appropriate high voltage circuitry to deliver a timed defibrillation pulse. While coil electrode 53 is depicted coupled to a portion of RV lead 32, such an electrode may be coupled to other portions of any of the leads depicted in FIG. 2, such as LV electrode 57. The coil electrode 53, subcutaneous electrode 45 or other types of suitable electrode configurations may be electrically coupled to low voltage pacing/sensing circuitry in addition to high voltage circuitry. As is known, such electrodes may be disposed in a variety of locations in, around, and on the heart.

Also depicted in FIG. 2 is an SQ sensor 44, an RV sensor 55 and an LV sensor 59 which may comprise one or more of a variety of sensors as is known in the art. Preferably RV sensor 55 comprises an absolute pressure sensor, but other pressure sensors may be utilized. In addition, RV sensor 55 and SQ sensor 44 may comprise an accelerometer, an impedance electrode, a saturated oxygen sensor, a pH sensor, and the like. In addition, each of the leads could carry a mechanical sensor for developing systolic and diastolic pressures and a series of spaced apart impedance sensing leads for developing volumetric measurements of the expansion and contraction of the RA, LA, RV, and LV.

Of course, such sensors must be rendered biocompatible and reliable for long-term use. With respect to embodiments of the invention delivering NES therapy, the preferred location for at least one electrode is within the heart, in close proximity to the myocardial tissue. In addition, one or more sensors may be disposed in or on the housing 20 of IMD 14 such as sensor 11 depicted in FIG. 2.

Figure 3A:
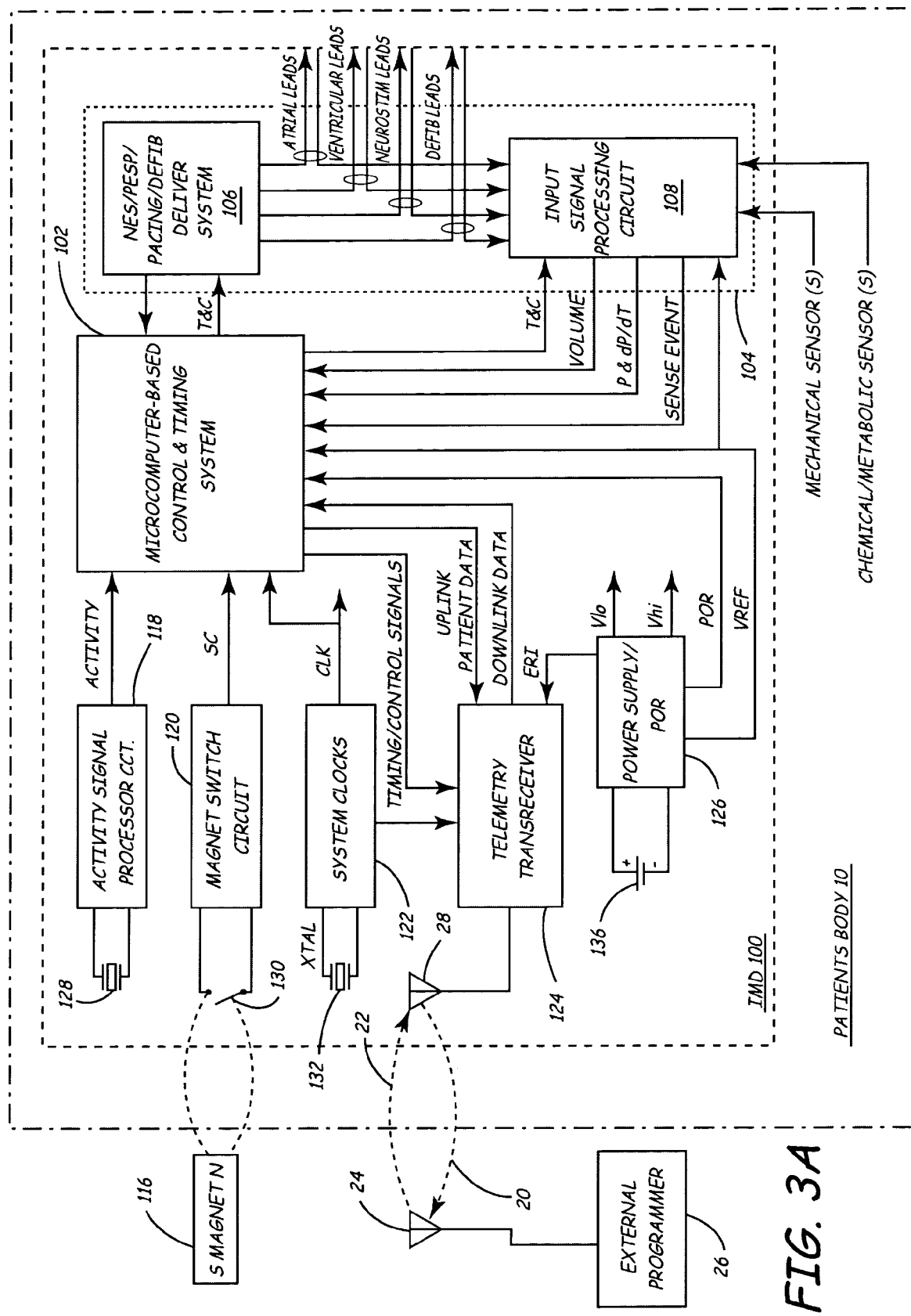
FIG. 3 is a simplified block diagram of one embodiment of IPG circuitry and associated leads employed in the system of FIG. 1 enabling selective therapy delivery and heart failure state monitoring in one or more heart chambers.

FIG. 3A depicts a system architecture of an exemplary multi-chamber IMD 100 implanted into a patient's body 10 that provides delivery of a therapy and/or physiologic input signal processing. The typical multi-chamber IMD 100 has a system architecture that is constructed about a microcomputer-based control and timing system 102 that varies in sophistication and complexity depending upon the type and functional features incorporated therein. The functions of microcomputer-based multi-chamber monitor/sensor control and timing system 102 are controlled by firmware and programmed software algorithms stored in RAM and ROM including PROM and EEPROM and are carried out using a CPU, ALU, etc., of a typical microprocessor core architecture. Of course, such firmware and software may be modified in situ (e.g., in vivo) and the operational characteristics may be adapted for a particular situation or patient. A physician or clinician may change one or more parameters, which will cause a change in the detection or response of such algorithms. Oftentimes, discrete values may be changed such that a desired software routine is advantageously altered, although sometimes an entirely new set of operating software may be substituted for an existing set of operating software, as is known in the art. The microcomputer-based multi-chamber monitor/sensor control and timing system 102 may also include a watchdog circuit, a DMA controller, a block mover/reader, a CRC calculator, and other specific logic circuitry coupled together by on-chip data bus, address bus, power, clock, and control signal lines in paths or trees in a manner well known in the art. It will also be understood that control and timing of multi-chamber monitor/sensor 100 can be accomplished with dedicated circuit hardware or state machine logic rather than a programmed microcomputer.

The multi-chamber monitor/sensor 100 also typically includes patient interface circuitry 104 for receiving signals from sensors and pace/sense electrodes located at specific sites of the patient's heart chambers and/or delivering PESP stimulation to derive heart failure parameters or a pacing therapy to the heart chambers. The patient interface circuitry 104 therefore comprises a PESP stimulation delivery system 106 optionally including pacing and other stimulation therapies and a physiologic input signal processing circuit 108 for processing the blood pressure and volumetric signals output by sensors. For purposes of illustration of the possible uses of embodiments of the invention, a set of lead connections are depicted for making electrical connections between the therapy delivery system 106 and the input signal processing circuit 108 and sets of pace/sense electrodes located in operative relation to the RA, LA, RV and LV. Alternatively, SQ leads may be included.

As depicted in FIG. 3A, chemical/metabolic sensor input and/or mechanical sensor inputs are provided to the input signal processing circuit 108. As described with respect to FIG. 2, a wide variety of such sensors may be utilized when practicing embodiments of the invention.

A battery provides a source of electrical energy to power the multi-chamber monitor/sensor operating system including the circuitry of multi-chamber monitor/sensor 100 and to power any electromechanical devices, e.g., valves, pumps, etc. of a substance delivery multi-chamber monitor/sensor, or to provide electrical stimulation energy of an ICD shock generator, cardiac pacing pulse generator, or other electrical stimulation generator. The typical energy source is a high energy density, low voltage battery 136 coupled with a power supply/POR circuit 126 having power-on-reset (POR) capability. The power supply/POR circuit 126 provides one or more low voltage power Vlo, the POR signal, one or more VREF sources, current sources, an elective replacement indicator (ERI) signal, and, in the case of an ICD, high voltage power Vhi to the therapy delivery system 106.

In order for the exemplary circuit of FIG. 3A to implement NES and/or PESP therapy or cardiac defibrillation therapy according to embodiments of the invention, the therapy delivery system 106 needs to utilize appropriate NES and/or PESP therapy and high voltage circuitry, respectively. If an NES therapy delivery electrode is disposed remotely from the heart the delivery of NES therapy may occur independent of the cardiac cycle (e.g., periodically approximately between 10 ms and about ten seconds). While many different types of pulses may be employed for NES therapy, one or more pulses of about 0.1 to about 10 ms duration have been shown to provide the desired results. Effective NES therapy may be delivered using a variety of electrode configuration (e.g., between one and several discrete electrodes). Also, standard tip, ring, coil, can, and subcutaneous electrodes may be utilized to effectively deliver NES therapy. While not specifically depicted in the drawings, suitable external circuitry may be adapted for NES therapy delivery including use of surface electrode patches, pads or paddles as well as pericardial electrodes. In particular, one or more electrodes disposed in the pericardial sac will be well positioned to stimulate cardiac tissue and the sympathetic nerves.

Virtually all current electronic multi-chamber monitor/sensor circuitry employs clocked CMOS digital logic ICs that require a clock signal CLK provided by a piezoelectric crystal 132 and system clock 122 coupled thereto as well as discrete components, e.g., inductors, capacitors, transformers, high voltage protection diodes, and the like that are mounted with the ICs to one or more substrate or printed circuit board. In FIG. 3A, each CLK signal generated by system clock 122 is routed to all applicable clocked logic via a clock tree. The system clock 122 provides one or more fixed frequency CLK signal that is independent of the battery voltage over an operating battery voltage range for system timing and control functions and in formatting uplink telemetry signal transmissions in the telemetry I/O circuit 124.

The RAM registers may be used for storing data compiled from sensed cardiac activity and/or relating to device operating history or sensed physiologic parameters for uplink telemetry transmission on receipt of a retrieval or interrogation instruction via a downlink telemetry transmission. The criteria for triggering data storage can also be programmed in via downlink telemetry transmitted instructions and parameter values The data storage is either triggered on a periodic basis or by detection logic within the physiologic input signal processing circuit 108 upon satisfaction of certain programmed-in event detection criteria. In some cases, the multi-chamber monitor/sensor 100 includes a magnetic field sensitive switch 130 that closes in response to a magnetic field, and the closure causes a magnetic switch circuit to issue a switch closed (SC) signal to control and timing system 102 which responds in a magnet mode. For example, the patient may be provided with a magnet 116 that can be applied over the subcutaneously implanted multi-chamber monitor/sensor 100 to close switch 130 and prompt the control and timing system to deliver a therapy and/or store physiologic episode data when the patient experiences certain symptoms. In either case, event related data, e.g., the date and time, may be stored along with the stored periodically collected or patient initiated physiologic data for uplink telemetry in a later interrogation session.

In the multi-chamber IMD 100, uplink and downlink telemetry capabilities are provided to enable communication with either a remotely located external medical device or a more proximal medical device on the patient's body or another multi-chamber monitor/sensor in the patient's body as described above with respect to FIG. 2 and FIG. 3A (and FIG. 3B described below). The stored physiologic data of the types described above as well as real-time generated physiologic data and non-physiologic data can be transmitted by uplink RF telemetry from the multi-chamber monitor/sensor 100 to the external programmer or other remote medical device 26 in response to a downlink telemetered interrogation command. The real-time physiologic data typically includes sampled signal waveforms (e.g., intracardiac EGM or pressure waveforms), waveform derived parameters (e.g. ePAD, dP/dtmax, or intracardiac electrocardiogram amplitude values), and sensor output signals. The non-physiologic patient data includes currently programmed device operating modes and parameter values, battery condition, device ID, patient ID, implantation dates, device programming history, real time event markers, and the like. In the context of implantable pacemakers and ICDs, such patient data includes programmed sense amplifier sensitivity, pacing or cardioversion pulse amplitude, energy, and pulse width, pacing or cardioversion lead impedance, and accumulated statistics related to device performance, e.g., data related to detected arrhythmia episodes and applied therapies. The multi-chamber monitor/sensor thus develops a variety of such real-time or stored, physiologic or non-physiologic, data, and such developed data is collectively referred to herein as "patient data".

The physiologic input signal processing circuit 108 therefore includes at least one electrical signal amplifier circuit for amplifying, processing and in some cases detecting sense events from characteristics of the electrical sense signal or sensor output signal. The physiologic input signal processing circuit 108 in multi-chamber monitor/sensors providing dual chamber or multi-site or multi-chamber monitoring and/or pacing functions includes a plurality of cardiac signal sense channels for sensing and processing cardiac signals from sense electrodes located in relation to a heart chamber. Each such channel typically includes a sense amplifier circuit for detecting specific cardiac events and an EGM amplifier circuit for providing an EGM signal to the control and timing system 102 for sampling, digitizing and storing or transmitting in an uplink transmission. Atrial and ventricular sense amplifiers include signal processing stages for detecting the occurrence of a P-wave or R-wave, respectively and providing an ASENSE or VSENSE event signal to the control and timing system 102. Timing and control system 102 responds in accordance with its particular operating system to deliver or modify a pacing therapy, if appropriate, or to accumulate data for uplink telemetry transmission or to provide a Marker Channel® signal in a variety of ways known in the art.

In addition, the input signal processing circuit 108 includes at least one physiologic sensor signal-processing channel for sensing and processing a sensor-derived signal from a physiologic sensor located in relation to a heart chamber or elsewhere in the body.

Figure 3B:
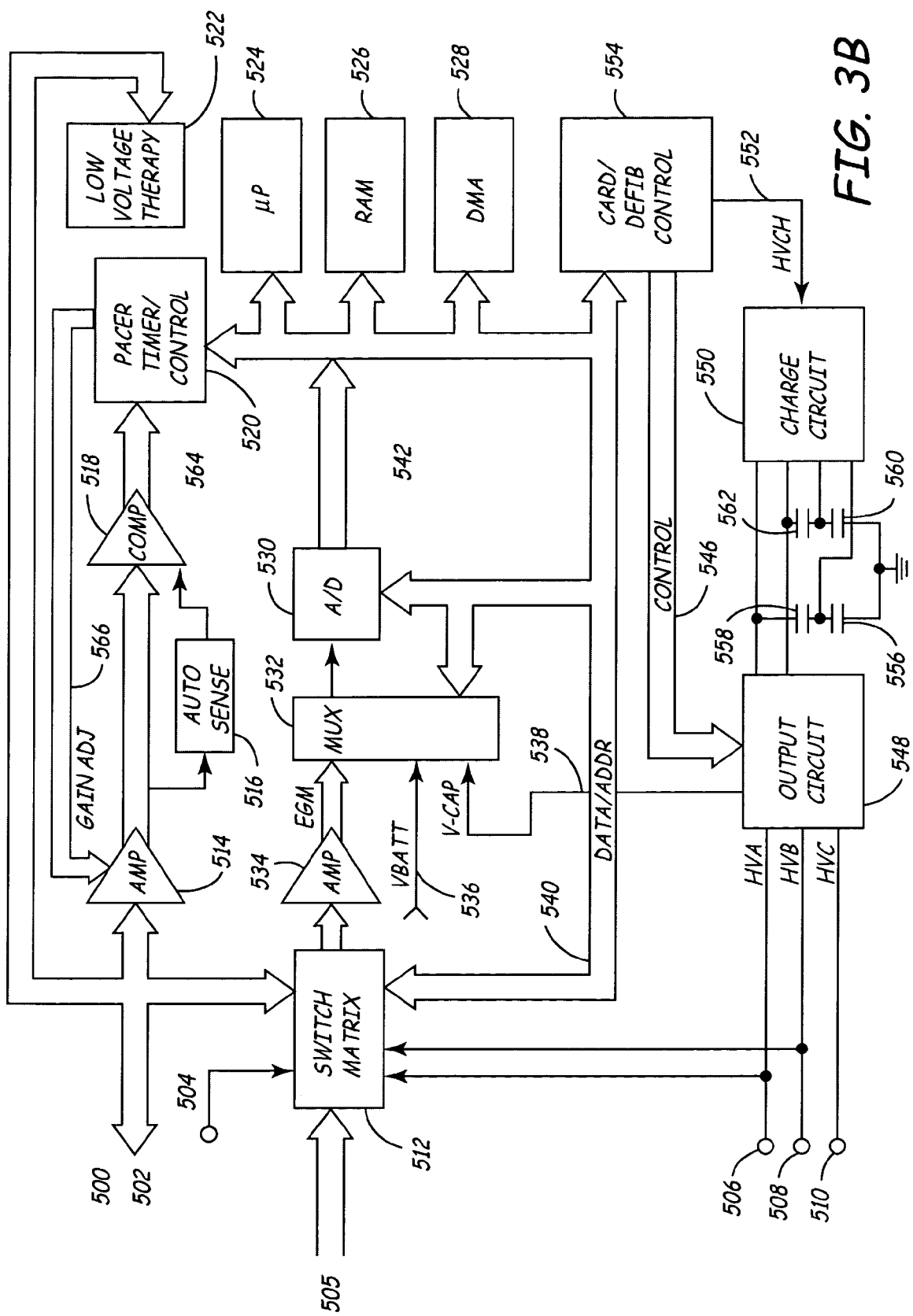

Now turning to FIG. 3B, another system architecture for use in conjunction with embodiments of the invention is depicted. FIG. 3B is an exemplary system that may be utilized to deliver therapy by incorporating the system and method described above. Notably, the depicted system includes a sense amplifier 534 to sense electrical signals such as EGM signals using one or more leads placed within a respective chamber of the heart. These signals are used to determine atrial and ventricular depolarizations and Q-T length so that NES and PESP delivery is provided in an optimized manner. One or more physiologic or hemodynamic signals may be sensed using sensors such as those discussed above. These additional signals, which are shown collectively provided on line 505, may be used to determine cardiac output so that therapy may be initiated, terminated, and/or optimized.

The system of FIG. 3B further includes a timer/controller to control the delivery of pacing pulses on output lines 500 and 502. This circuit, alone or in conjunction with microprocessor 524, controls interval lengths, pulse amplitudes, pulse lengths, and other waveform attributes associated with the NES and PESP pulses. Output circuit 548 delivers high-voltage stimulation such as defibrillation shocks under the control of defibrillation control circuit 554.

Not all of the conventional interconnections of these voltages and signals are shown in either FIG. 3A or FIG. 3B and many other variations on the illustrated electronic circuitry are possible, as is known to those of skill in the art.

Figure 4:
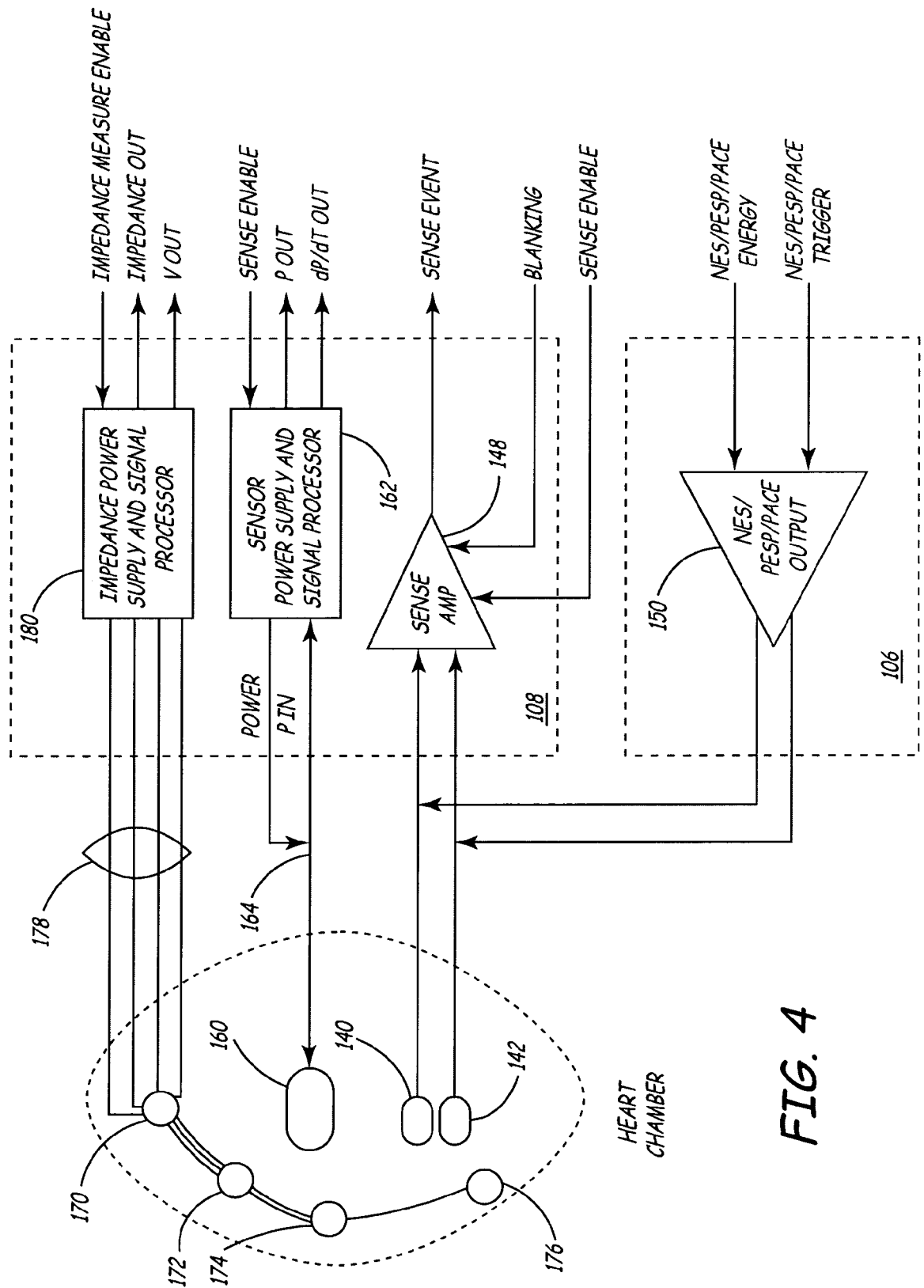
FIG. 4 is a simplified block diagram of a single monitoring and pacing channel for deriving pressure, impedance and cardiac EGM signals employed in monitoring HF and optionally pacing the heart and delivering PESP therapy in accordance with embodiments of the invention.

FIG. 4 schematically illustrates one pacing, sensing, and parameter measuring channel in relation to one heart chamber. A pair of pace/sense electrodes 140, 142, a sensor 160 (e.g., a pressure, saturated oxygen, flow, pH or the like), and a plurality, e.g., four, impedance-measuring electrodes 170, 172, 174, 176 are located in operative relation to the heart chamber. The pair of pace/sense electrodes 140, 142 are located in operative relation to the heart chamber and coupled through lead conductors 144 and 146, respectively, to the inputs of a sense amplifier 148 located within the input signal processing circuit 108. The sense amplifier 148 is selectively enabled by the presence of a sense enable signal that is provided by control and timing system 102. The sense amplifier 148 is enabled during prescribed times when pacing is either enabled or not enabled as described below in reference to the measurement of the parameters of heart failure. The blanking signal is provided by control and timing system 102 upon delivery of a pacing pulse, PESP pulse, or NES pulse train to disconnect the sense amplifier inputs from the lead conductors 144 and 146 for a short blanking period in a manner well known in the art. When sense amplifier 148 is enabled and is not blanked, it senses the electrical signals of the heart, referred to as the EGM, in the heart chamber. The sense amplifier provides a sense event signal signifying the contraction of the heart chamber commencing a heart cycle based upon characteristics of the EGM, typically the P-wave when the heart chamber is the RA or LA and the R-wave, when the heart chamber is the RV or LV, in a manner well known in the pacing art. The control and timing system responds to non-refractory sense events by restarting an escape interval (EI) timer timing out the EI for the heart chamber, in a manner well known in the pacing art.

The pair of pace/sense electrodes 140, 142 are also coupled through lead conductors 144 and 146, respectively, to the output of a pulse generator 150. The pulse generator 150, within NES/PESP/pacing delivery system 106, selectively provides a pacing pulse to electrodes 140, 142 in response to a NES/PESP/PACE trigger signal generated at the time-out of the EI timer within control and timing system 102 in a manner well known in the pacing art. Or, the pulse generator 150 selectively provides a PESP pulse or pulse train to electrodes 140, 142 in response to a NES/PESP/PACE trigger signal generated at the time-out of an ESI timer within control and timing system 102 in the manner described in the above-referenced '098 patent to cause the heart chamber to contract more forcefully, the increased force depending upon the duration of the ESI.

The sensor 160 and/or other physiologic sensor is coupled to a sensor power supply and signal processor 162 within the input signal processing circuit 108 through a set of lead conductors 164 that convey power to the sensor 160 and sampled blood pressure P signals from the sensor 160 to the sensor power supply and signal processor 162. The sensor power supply and signal processor 162 samples the blood pressure impinging upon a transducer surface of the sensor 160 located within the heart chamber when enabled by a sense enable signal from the control and timing system 102. As an example, absolute pressure P, developed pressure DP and pressure rate of change dP/dt sample values can be developed by sensor power supply and signal processor unit 162 or by the control and timing system 102 for storage and processing as described further below. The sensor 160 and a sensor power supply and signal processor 162 may take the form disclosed in commonly assigned U.S. Pat. No. 5,564,434.

The set of impedance electrodes 170, 172, 174 and 176 is coupled by a set of conductors 178 and is formed as a lead that is coupled to the impedance power supply and signal processor 180. Impedance-based measurements of cardiac parameters such as stroke volume are known in the art such as having an impedance lead having plural pairs of spaced surface electrodes located within the heart chamber. The spaced apart electrodes can also be disposed along impedance leads lodged in cardiac vessels, e.g., the coronary sinus and great vein or attached to the epicardium around the heart chamber. The impedance lead may be combined with the pace/sense and/or pressure sensor bearing lead.

A measure of heart chamber volume V is provided by the set of impedance electrodes 170, 172, 174 and 176 when the impedance power supply and signal processor 180 is enabled by an impedance measure enable signal provided by control and timing system 102. A fixed current carrier signal is applied between the pairs of impedance electrodes and the voltage of the signal is modulated by the impedance through the blood and heart muscle which varies as distance between the impedance electrodes varies. Thus, the calculation of the heart chamber volume V signals from impedance measurements between selected pairs of impedance electrodes 170, 172, 174 and 176 occurs during the contraction and relaxation of the heart chamber that moves the spaced apart electrode pairs closer together and farther apart, respectively, due to the heart wall movement or the tidal flow of blood out of and then into the heart chamber. Raw signals are demodulated, digitized, and processed to obtain an extrapolated impedance value. When this value is divided into the product of blood resistivity times the square of the distance between the pairs of spaced electrodes, the result is a measure of instantaneous heart chamber volume V within the heart chamber.

In accordance with embodiments of the invention, the IMD measures a group of parameters indicative of the state of heart failure or physiologic state employing EGM signals, measures of absolute blood pressure P and/or dP/dt, saturated oxygen, flow, pH or the like and measures of heart chamber volume V over one or more cardiac cycles. These parameters are determined periodically throughout each day regardless of patient posture and activity. However, the patient may be advised by the physician to undertake certain activities or movements at precise times of day or to simultaneously initiate the determination of the parameters though use of a magnet or a remote system programmer unit (not depicted) that is detected by the IMD. Certain of the parameters are only measured or certain of the parameter data are only stored when the patient heart rate is within a normal sinus range between programmed lower and upper heart rates and the heart rhythm is relatively stable. The parameter data and related data, e.g., heart rate and patient activity level, are date and time stamped and stored in IMD memory for retrieval employing conventional telemetry systems. Incremental changes in the stored data over time provide a measure of the degree of change in the heart failure condition of the heart. Such parameter data and related data may be read, reviewed, analyzed and the like and the parameter data may be changed based on a current patient condition, a patient history, patient or physician preference(s) and the like.

Figure 5:
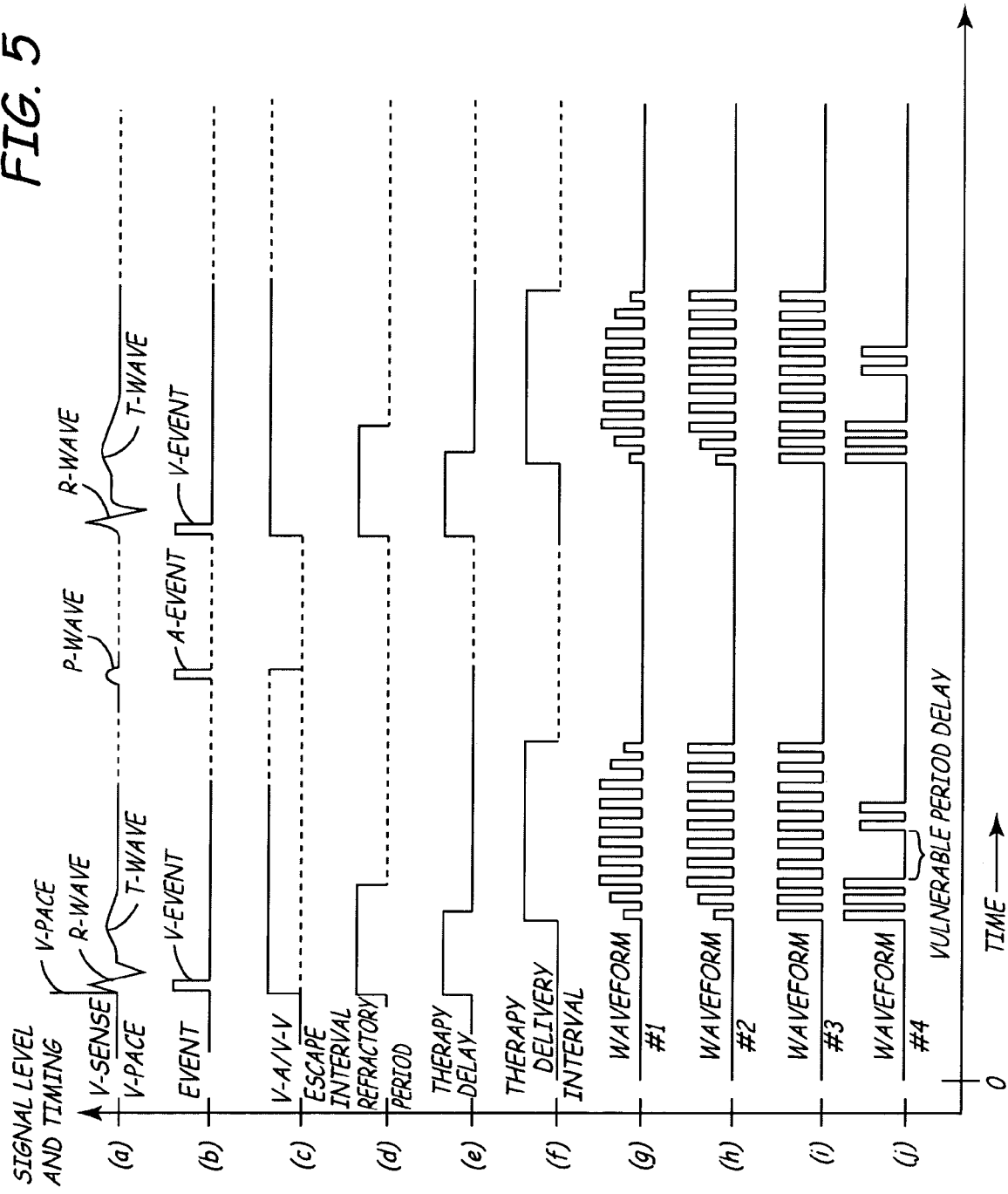
FIG. 5 depicts the delivery of therapeutic PESP stimulation, particularly, pacing energy pulse trains commenced during the refractory period of the heart and continuing for a PESP delivery interval.

Turning to FIG. 5, the general timing diagram illustrates the timing of delivery of PESP and NES stimulation in relation to a timed interval from a sensed or paced event as well as alternative pulse waveforms of the PESP and NES stimulation. In accordance with one aspect of embodiments of the invention, a therapeutic stimulation delay illustrated in tracing (e) is timed out from a sensed or paced event (e.g., the illustrated V-EVENTs) that for NES starts with the sensed or paced event and is shorter than the refractory period of the heart. An NES stimulus pulse train is delivered to the ventricles in the depicted therapy delivery interval of tracing (f) commencing after time-out of the delay and before the end of the refractory period so that the delivery of the NES therapy falls within the refractory period. The pulses for PESP therapy delivery are intended to be suprathreshold in nature, and therefore must be of sufficient energy to depolarize the heart when they are delivered in the non-refractory period of the heart cycle so that the heart is captured by at least one of the PESP pulses falling outside the refractory period. For simplicity of illustration, the tracings (f)-(j) are expanded in length, and the depolarization of the heart that they cause is not depicted in tracing (a). The amplitude and number of NES pulses and PESP pulses in each therapy pulse train and the spacing between the pulses may also differ from the illustrated tracings (g)-(j).

The ventricular sense or pace event detected in tracing (b) also triggers the timing out of an escape interval in tracing (c) which may be terminated by the sensing of a subsequent atrial or ventricular event, depending on the operating mode of the system. The first depicted sequence in FIG. 5 shows the full time-out of the escape interval in tracing (c), the refractory period in tracing (d), and the therapy delay and delivery intervals in tracings (e) and (f). The therapy delay and therapy delivery intervals can be derived as a function of an intrinsic V-V or V-A escape interval derived by measuring and averaging intervals between intrinsic ventricular and/or atrial sense events or paced events. The therapy delay can also be determined from a measurement of the Q-T interval and by sensor feedback (e.g. accelerometer or pressure) telling when capture occurred. As illustrated, the therapy delay in tracing (e) delays delivery of the therapy pulse train until the QRS complex ends or about 40-60 ms after the V-EVENT well before the start of the vulnerable period of the heart which occurs near the end of the T-wave.

The therapy delivery interval is timed to start any time after the V-event and end well before the end of the previously derived V-V or V-A escape interval. In this example, it is extended for ease of illustration of the pulse trains in tracings (f)-(j). The therapy delivery interval can be broken into NES and PESP therapy delivery intervals, separated by the end of the refractory period.

The therapy stimulation energy is delivered in the form of a burst of one or more constant or variable energy stimulation pulses separated by a pulse separation interval between each pulse of the burst and spanning in time through the therapy delivery interval. All of the pulses can have the same amplitude and energy as shown in waveform 3 of tracing (i). Or the leading and/or trailing pulses of the pulse train can have ramped amplitudes similar to the waveform 1 illustrated in tracings (g). In tracing (g), the ramp down trailing edge amplitudes of a further sub-set of the pulses of the burst is shown decreasing from the maximum amplitude to terminating amplitude. This embodiment would allow for delivery of higher energy NES pulses when the tissue is known to be refractory, followed by delivery of progressively lower energy pulses (that may still be producing NES effects) as the refractory period nears (and arrhythmia induction risk increases). Ultimately, one of the pulses will capture the heart once the refractory period ends, at which point the therapy pulses would be stopped. This would result in continuous NES therapy delivery until the earliest possible PESP pulse is evoked.

The initial set of NES pulses delivered during the refractory period can have a higher pulse amplitude or width as shown in the waveforms. The high-energy pulses delivered during the refractory period can enhance potentiation during subsequent heart cycles. Tracing (j) also illustrates alternative numbers and spacing of the pulses of the pulse train, and it will be understood that this embodiment can also employ one or more pulses on either side of the delay.

In addition, it may be desirable to avoid delivering any therapy pulses in the vulnerable period of the heart near the end of the T-wave, particularly if high-energy pulses are delivered during the refractory period. Tracing (j) also illustrates a vulnerable period delay between the high energy NES pulses delivered during the refractory period and the lower energy PESP pulses after the refractory period to avoid delivering any pulses during the vulnerable period of the heart. It would also be possible to lower the pulse energy of the pulses delivered later in the refractory period. Tracing (i) of waveform 3 also shows the PESP therapy being halted due to a sensed event.

The therapy delivery capability is preferably implemented into a system that may include conventional operating modes for pacing and CRT (cardiac resynchronization therapy) therapies as well as cardioversion/defibrillation capabilities or as a stand alone system for simply providing pulse therapies to effect potentiation of myocardial cells between sensed PQRST complexes shown in FIG. 5.

Figure 6:
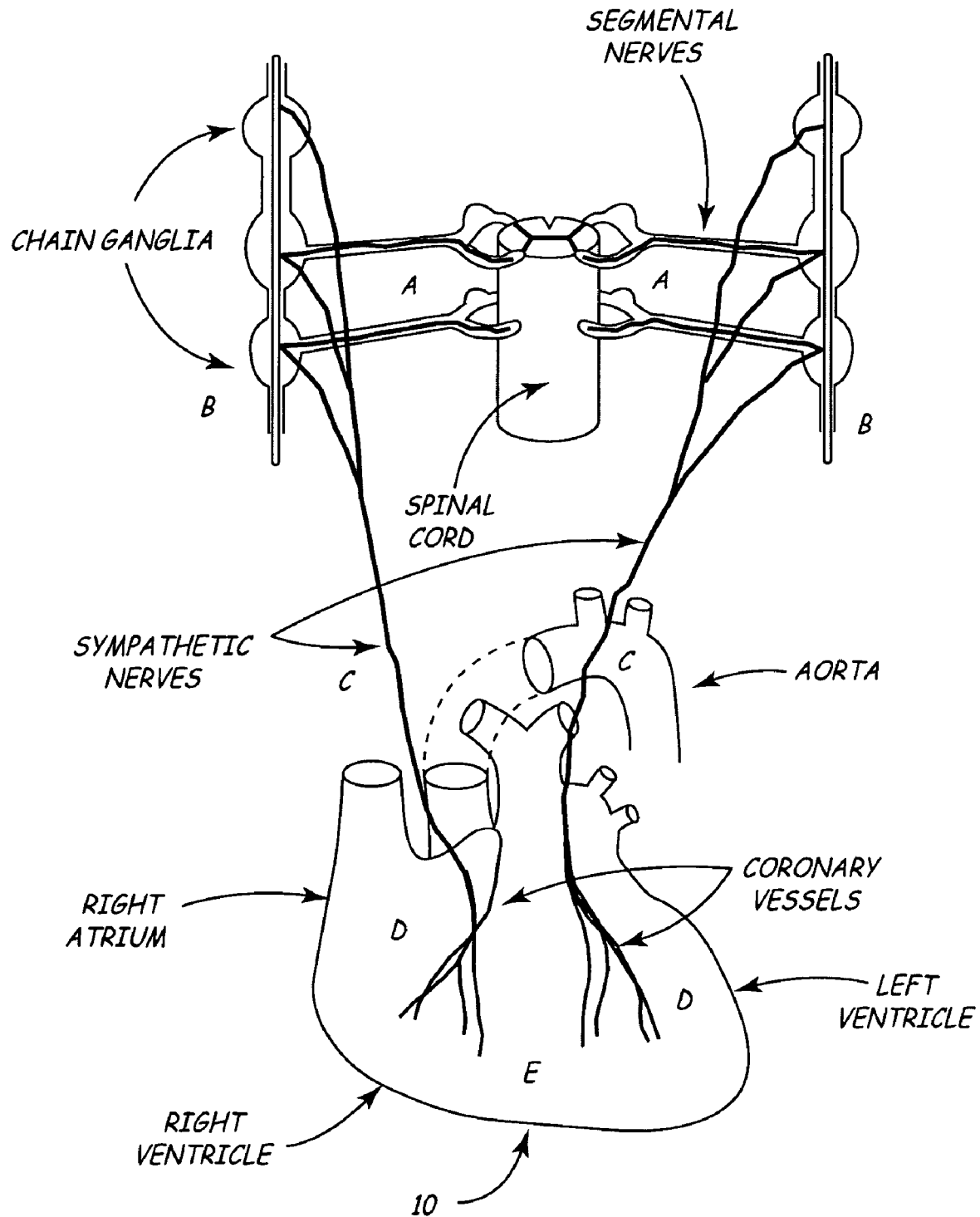
FIG. 6 is a perspective view with portions exploded (and with some portions not depicted) of a heart and related sympathetic nerves which may be advantageously stimulated according to certain embodiments of the invention.

Now turning to FIG. 6 in which sympathetic innervation of the heart and electrode locations for one aspect of nonexcitatory stimulation (NES), namely neural NES, is depicted in a partially exploded perspective view with portions removed for ease of inspection. Significant elements in FIG. 6 are identified as the following: spinal cord, cervical and thoracic segmental nerves (collectively denoted by the letter "A"), cervical and thoracic chain ganglia (up and down near the vertebral bodies at back of thorax (denoted with the letter "B"), autonomic nerves traveling through the thorax and mediastinum toward great vessels and the heart 10 and including the ansa subclavia (denoted with the letter "C"), various cardiac nerves often traveling near coronary vessels (denoted with the letter "D"), and cardiac nerves in the myocardium (denoted with the letter "E"). Electrodes (such as depicted in FIG. 2) may be positioned anywhere along these pathways to direct electrical stimulation current to these sympathetic nerves and avoid painful stimulation of other nerves or organs and avoid pacing the heart 10. Alternatively, subcutaneous electrodes such as the can electrode or other subcutaneous patch electrodes may be employed to stimulate broadly regions A-E and reserved for severe dysfunction including cardiogenic shock and electromechanical dissociation (EMD) or pulseless electrical activity (PEA). Furthermore, subcutaneous patch, pad electrodes or paddle electrodes may be similarly employed to direct electrical current to related sympathetic neural tissue in accordance with this aspect of embodiments of the invention. However, for the remaining discussion neural NES therapy is delivered to cardiac nerves via implanted electrodes such as those shown in FIG. 2.

Figure 7:
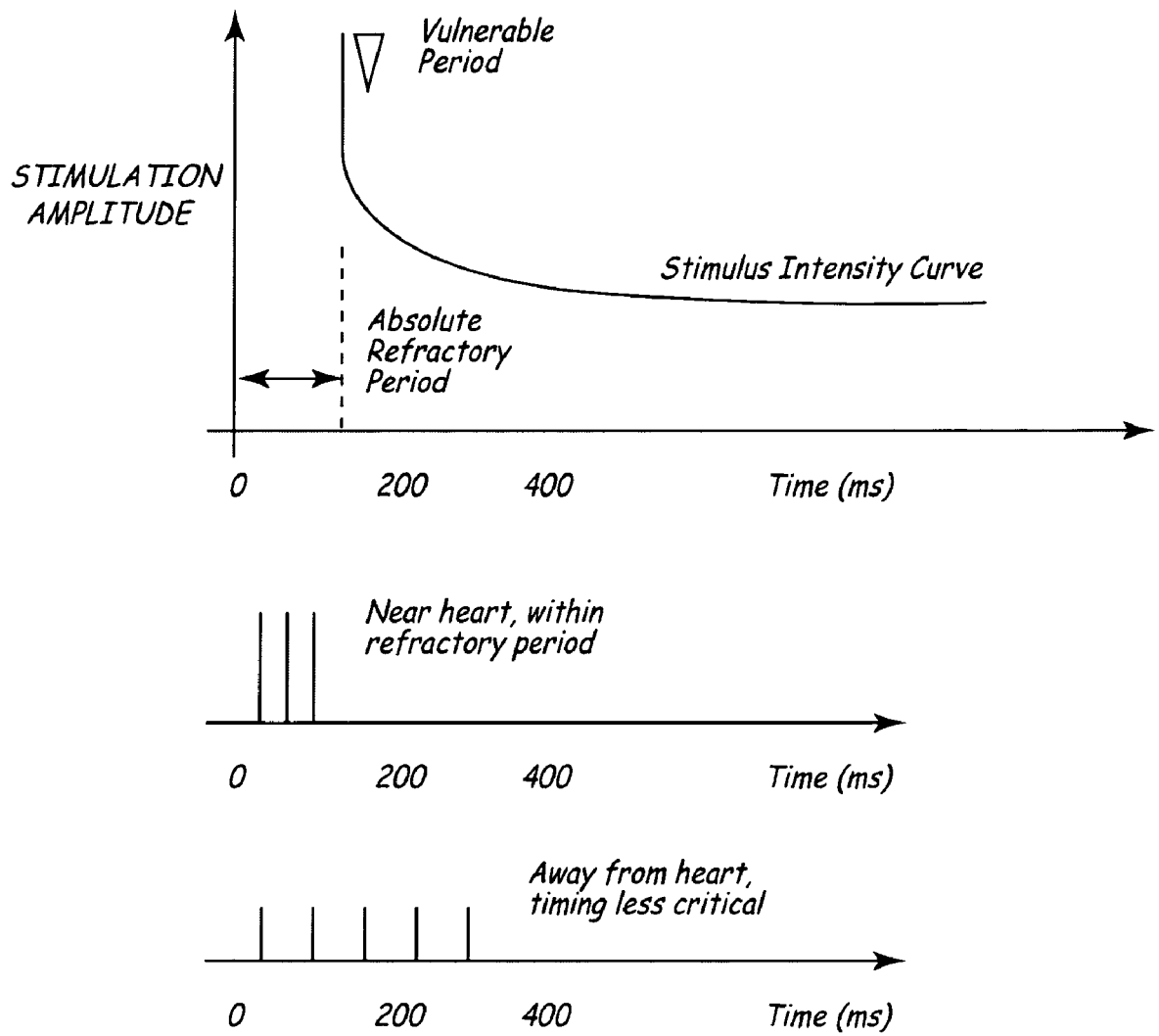
FIG. 7 is a depiction of NES timing for electrodes disposed near the cardiac tissue and relatively remotely from the cardiac tissue of a patient.

Now turning to FIG. 7, which depicts NES and the cardiac refractory period, it can be seen that a stimulation threshold curve of cardiac muscle and the electrode location for NES governs stimulation pulse timing. Adjacent to the heart tissue, where stimulation could directly affect the myocytes or cause capture, the NES pulses are delivered during the refractory period and/or remain subthreshold (i.e., below a threshold magnitude). Further from the cardiac tissue, where the effect would be primarily on the nerves depicted in FIG. 6, the stimulation pulses may have different amplitude and may be more widely spaced.

Figure 8:
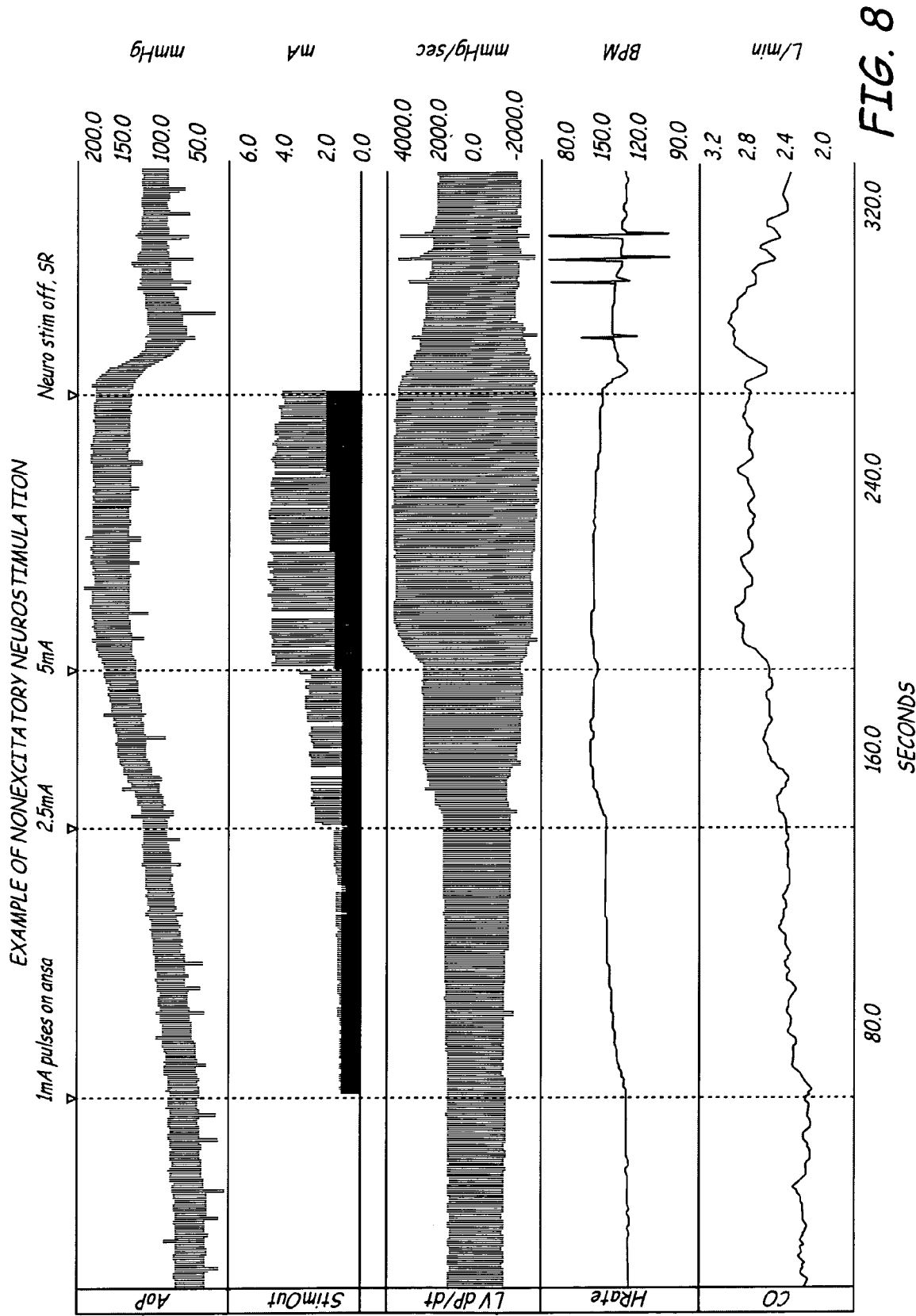
FIG. 8 is a set of traces representing physiologic and therapy activity according to embodiments of the invention.

FIG. 8 is a diagram illustrating an example of NES therapy delivery. This diagram illustrates the effects of stimulating sympathetic nerves near the heart with increasing amounts of current (1, 2.5, and 5 mA, respectively) using NES stimulation during the refractory period. Such NES stimulation results in a dose dependent increase of aortic blood pressure (AoP), contractility (LV dP/dt), heart rate, and cardiac output. The magnitude of the response may be similarly controlled by adjusting the duration and/or number of pulses in the NES pulse train. The NES therapy timing and stimulus parameters are preferably controlled by a microprocessor or hardware and programmable with input values determined by algorithms or clinicians, such as depicted in the system diagrams of FIG. 3A and FIG. 3B.

Figure 9:
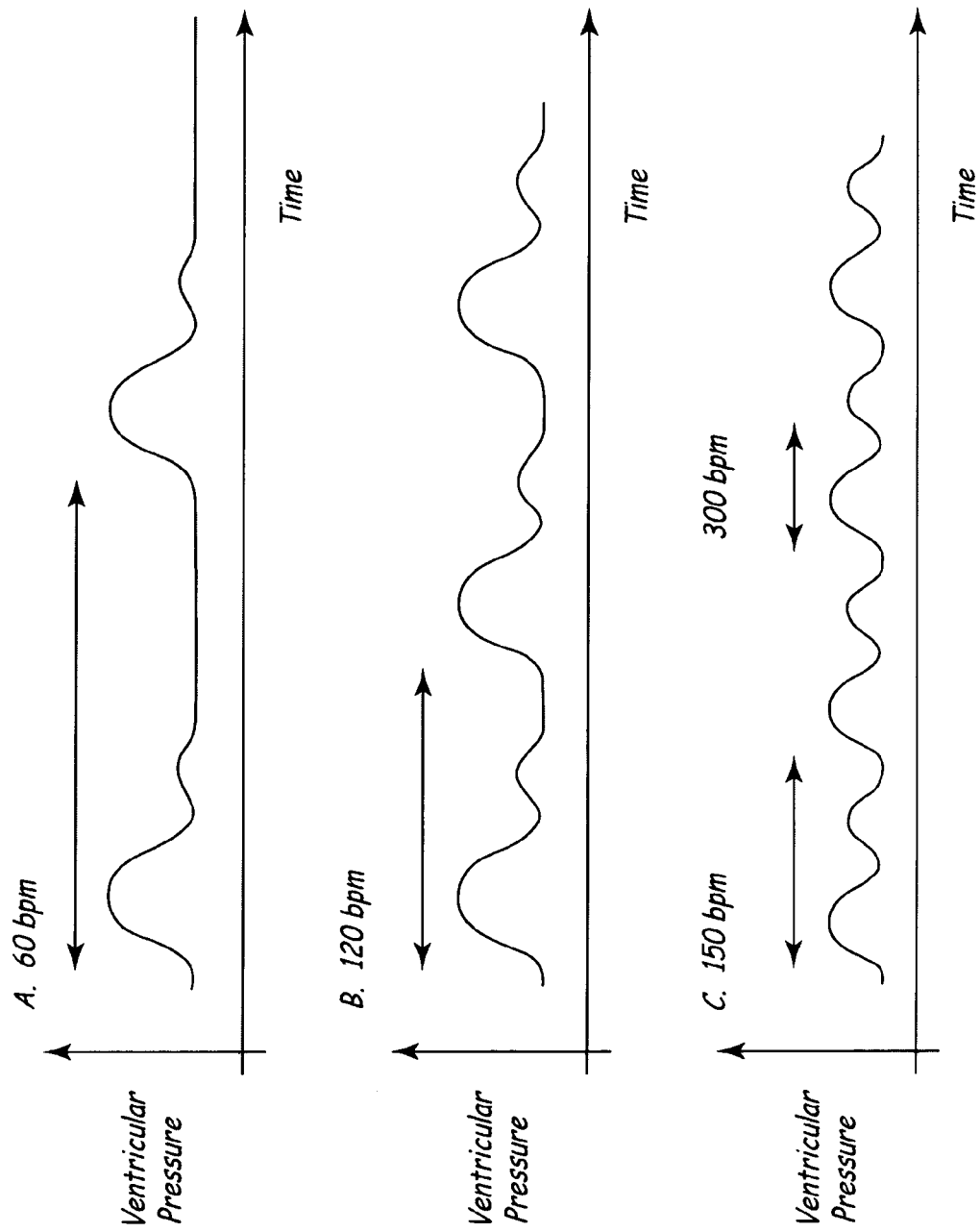
FIG. 9 is a set of three X-Y plots representing physiologic and therapy activity according to embodiments of the invention.

FIG. 9A through 9C illustrate the consequences of PESP stimulation during a tachycardia event. The inventors have discovered that it is helpful, if not absolutely necessary, to cease delivery of excitatory PESP stimulation therapy during tachycardias. In the condition depicted in FIG. 9A, the ventricular mechanical rate is low (60 bpm), the amplitude of the potentiation is large, and there is sufficient time in diastole for ventricular filling. In the condition depicted in FIG. 9B the heart rate has effectively doubled (i.e., increased to 120 bpm), and while the amplitude of potentiation remains large the diastolic time is shorter. In the condition depicted in FIG. 9C, the heart rate is even higher (i.e., at about 150 bpm) and the extrasystole encroaches severely on the cardiac cycle's time in diastole. Furthermore, at these high heart rates PESP potentiation diminishes. The PESP stimulation transforms the 150 bpm tachycardia to a ventricular tachycardia with mechanical alternans and an effective rate of 300 bpm. Heart rates this high are poorly tolerated and will further contribute to cardiac dysfunction, heart failure decompensation, and predispose a person subjected to such an effective heart rate to VT or VF. Likewise, it may be undesirable to apply NES at high heart rates.

Figure 10:
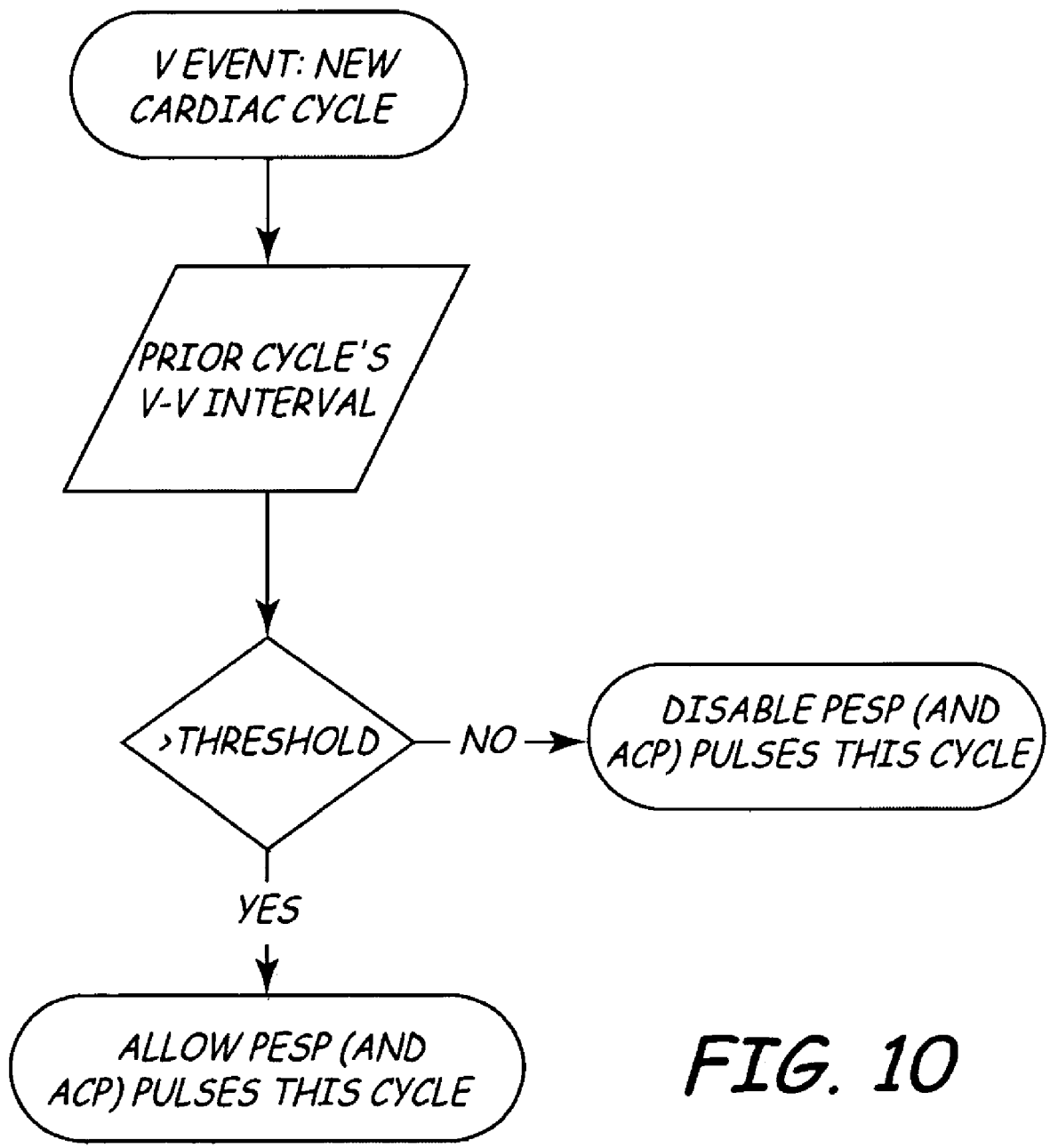
FIG. 10 is a flow chart depicting an aspect of embodiments of the invention.

Referring now to FIG. 10, a flow chart for a start-stop delivery lockout rule for application of PESP and NES stimulation is depicted. It can be appreciated that each new cardiac cycle begins with a ventricular event (Vevent) that is either a Vpace or Vsense. The therapy delivery lockout rule has veto power over the decision to deliver PESP and/or NES stimulation to the ventricle. If the prior V-V interval is greater than a threshold value, PESP and/or NES pulses are enabled for this cycle. Should the V-V interval be too short, stimulation therapy is aborted. This prevents stimulation therapy from further adding to the arrhythmic potential of an intrinsic premature ventricular contraction (PVC). Stimulation with a short coupling interval, particularly if immediately following other short intervals can be pro-arrhythmic and is, of course, to be avoided. The therapy delivery lockout rule also prevents application of PESP and/or NES therapy during various tachycardias including: sinus tachycardia, supraventricular tachycardia (SVT), ventricular tachycardia (VT), or ventricular fibrillation (VF). The threshold used may either be a fixed value or derived from other hemodynamic or electrogram based parameters and is typically 400-600 ms. The therapy delivery lockout rules may operate using a variety of timing schemes that are microprocessor or hardware controlled and programmable with input values determined by algorithms or clinicians, such as depicted in the system diagrams of FIG. 3A and FIG. 3B.

Figure 11:
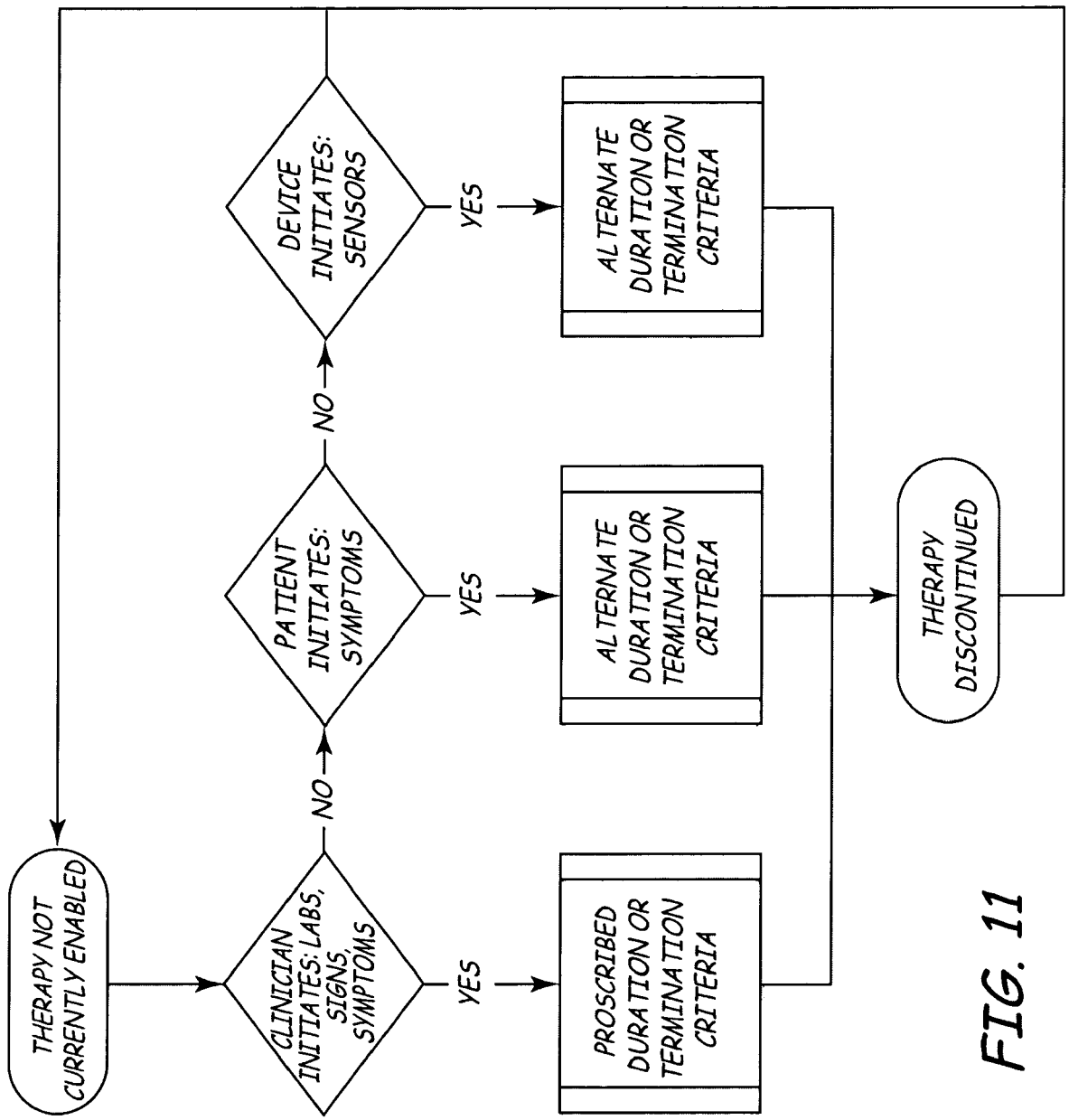
FIG. 11 is a flow chart depicting another aspect of embodiments of the invention.

Referring now to FIG. 11, which is a top-level flow chart governing initiation and termination of stimulation therapies according to embodiments of the invention. If therapy is not currently enabled, a clinician, the patient, or the device can initiate therapy. The clinician is able to preempt an assessment by the device or patient to begin stimulation therapy based on consultation with the patient, signs or symptoms of cardiac dysfunction, or lab results. If begun in this manner the therapy may have a duration and termination criteria different from patient or device initiated therapy. Similarly, the patient, as a result of symptoms or anticipated exertion may preempt the device and begin therapy. Finally, the device may automatically begin therapy based on preprogrammed time of day or due to sensor signals, including electograms, hemodynamic, activity sensor signals, and other physiologic sensor signals. Therapy may be discontinued by clinician command, patient request, or device based criteria that include sufficient therapy duration and sensor assessment of sufficient benefits or risks.

Figure 12:
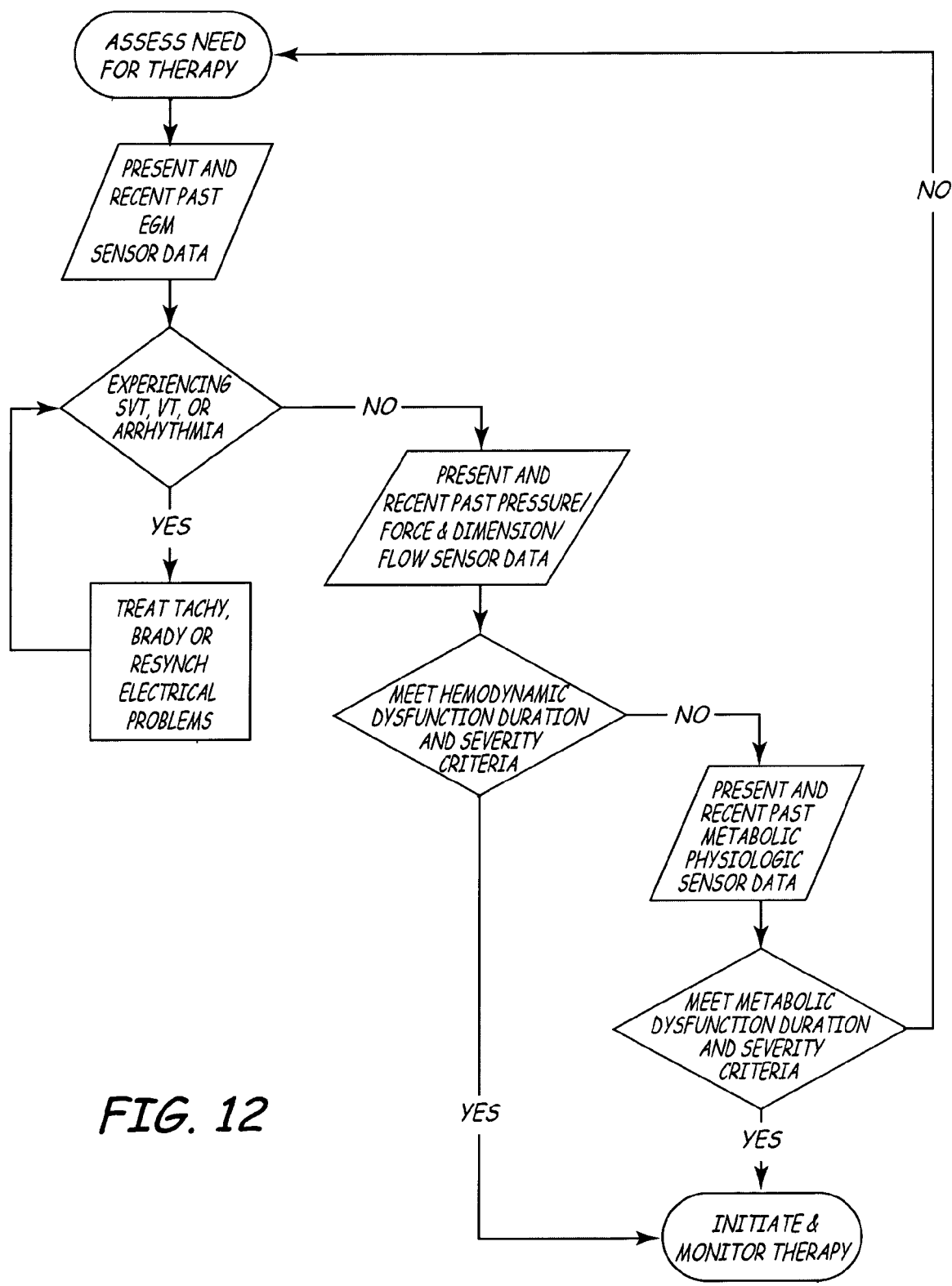
FIG. 12 is a flow chart depicting yet another aspect of embodiments of the invention.

In FIG. 12, a more detailed flow chart of automated sensor-governed initiation of stimulation therapies is shown. Therapy could remain on all the time, turned on periodically, or only when sensor indicates therapy is needed. The therapy could also be turned on for so many hours a day. Alternately, the therapy could be based on electrogram (EGM) sensor signals derived from a patient (both presently and recently), the device first looks for and treats cardiac rhythm problems before moving on to examine other sensor signal data. If the cardiac rhythm appears satisfactory, then hemodynamic sensors such as pressure and flow are employed. If there is sufficient dysfunction and duration, therapy begins. Metabolic or other physiologic sensor severity and duration assessments as well as a prescheduled time of day criteria may also initiate stimulation therapies according to the embodiments of the invention.

Figure 13:
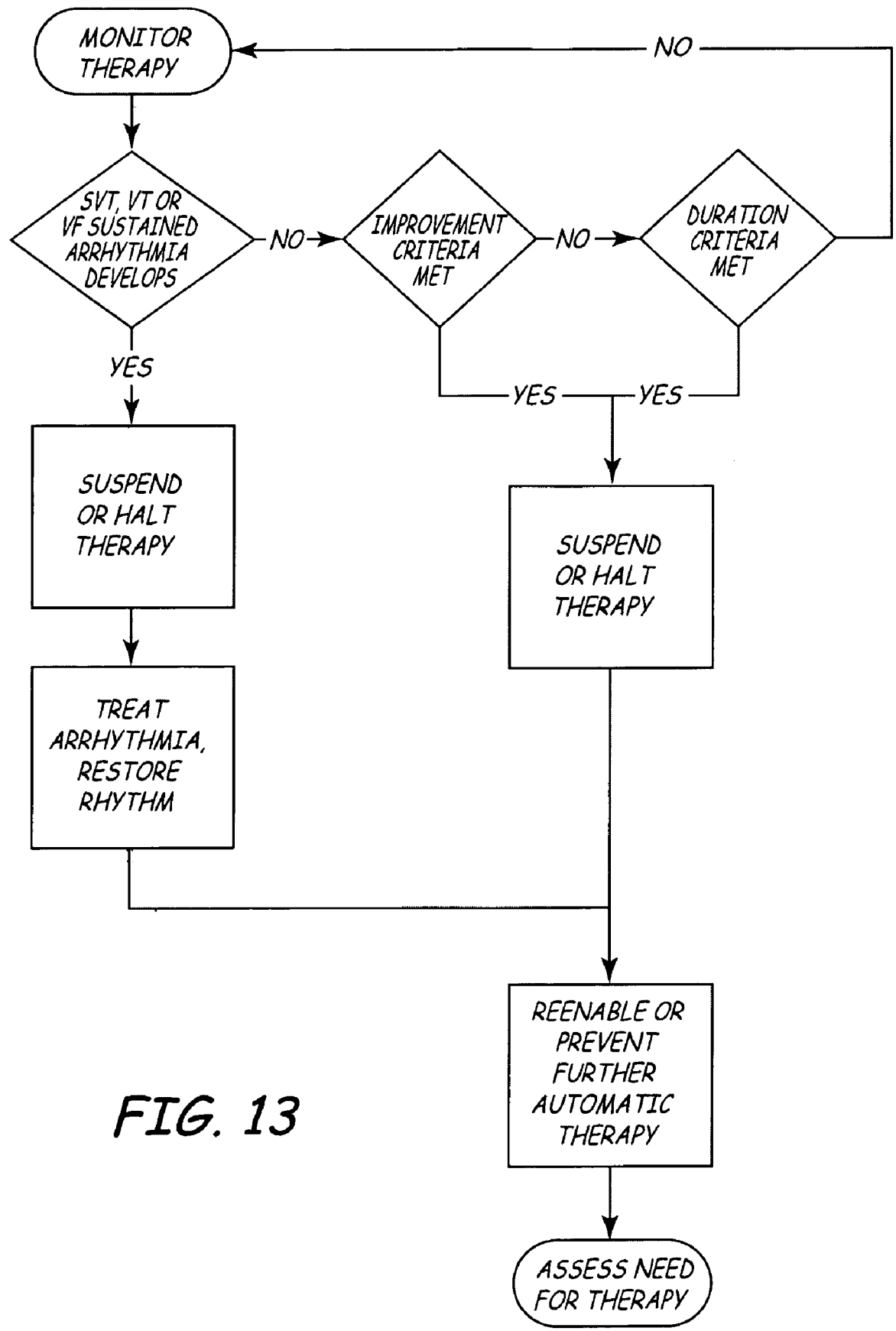
FIG. 13 is a flow chart depicting an additional aspect of embodiments of the invention.

With respect to FIG. 13, which is an expanded diagram of suspension or termination of stimulation therapies according to embodiments of the invention. If a tachyarrhythmia develops of sufficient rate or duration (e.g., which exceeds a predetermined rate or duration threshold), the therapy is either temporarily suspended or halted altogether and if necessary the arrhythmia treated by any of a variety of well-known means such as antitachycardia pacing (ATP), cardioversion, or the like. Upon restoration of a more normal rhythm, the device may or may not re-enable automatic therapy delivery. The device may also readjust its stimulation therapy parameters such as timing and amplitude to achieve a lower arrhythmia risk profile, trading physiologic benefit for arrhythmia risk (on the presumption that the stimulation therapies either caused or predisposed the subject to this arrhythmia). If the rhythm remains satisfactory, the device checks if either duration or combined hemodynamic improvement and duration criteria are met. If so, the therapies are again either temporarily suspended or halted altogether. Automated therapies may be re-enabled after a period of time or left disabled. In order to prevent multiple brief cyclic applications of therapy, the improvement criteria may be different from the initiation criteria to implement a hysteresis-like effect. Therapies may also be disabled upon reaching a fixed number of therapy applications and require an external override to restart.

Figure 14:
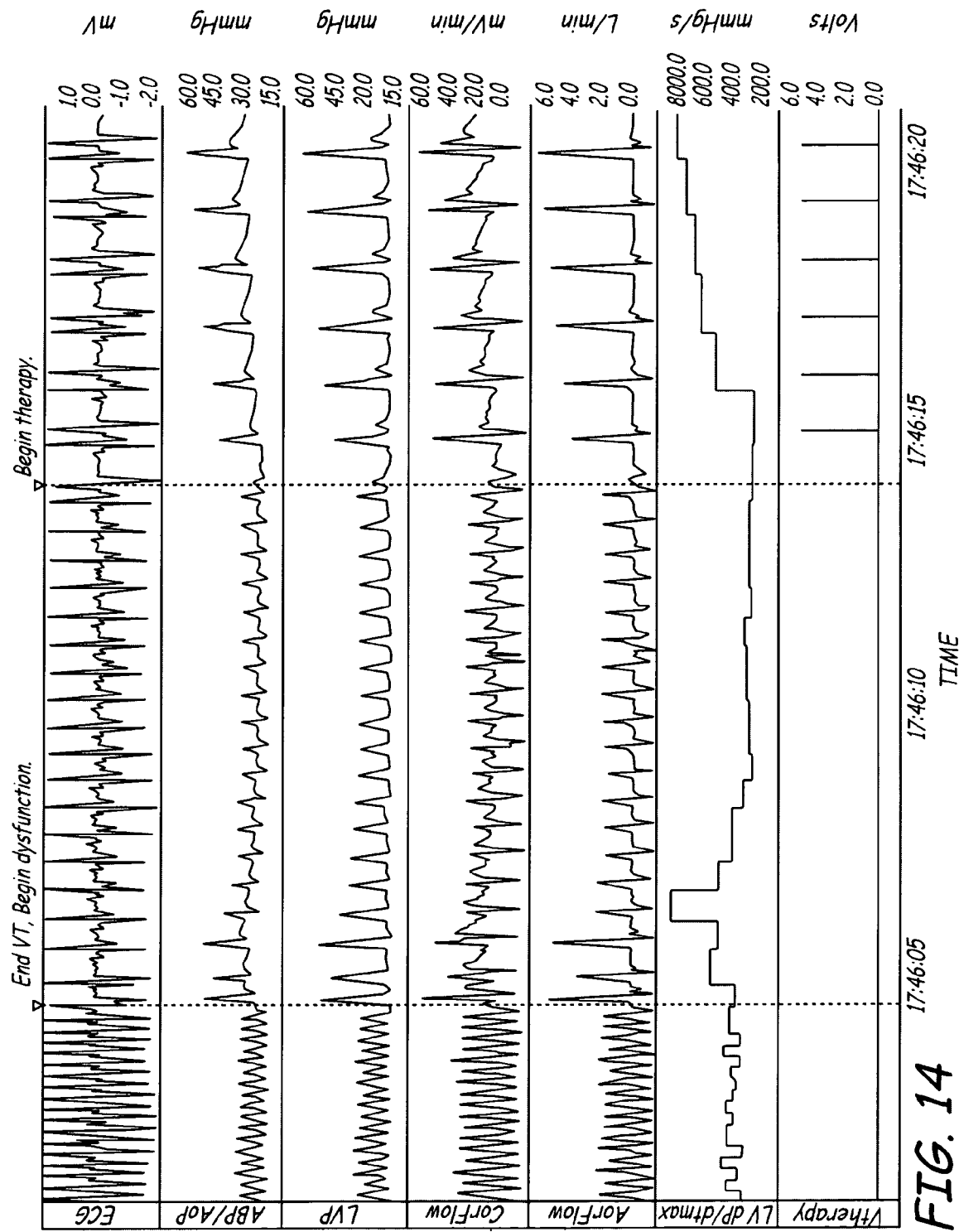
FIG. 14 is a set of traces representing physiologic and therapy activity according to embodiments of the invention.

Referring now to FIG. 14, which depicts termination of a tachyarrhythmia and initiation of therapy for cardiac dysfunction, FIG. 14 illustrates of the therapy initiation rules described above. As can be seen with reference to FIG. 14, a tachyarrhythmia is ended at about 17:46:05 and electrogram sensors (here the surface electrocardiogram (ECG)) confirm the existence of a reasonable rhythm and rate. However, hemodynamic sensors such as arterial blood pressure (ABP) and left ventricular pressure (LVP) confirm a severe level of dysfunction (e.g. LV dP/dtmax<400 mmHg/s) that is sustained for over 6 seconds and over 12 cardiac cycles. As a result, the decision to initiate PESP stimulation therapy occurs at about 17:46:15. A prompt response of arterial blood pressure, LVP, coronary blood flow, aortic blood flow, and LV dP/dtmax is seen coincident with the application of PESP therapy pulses (Vtherapy).

Figure 15:
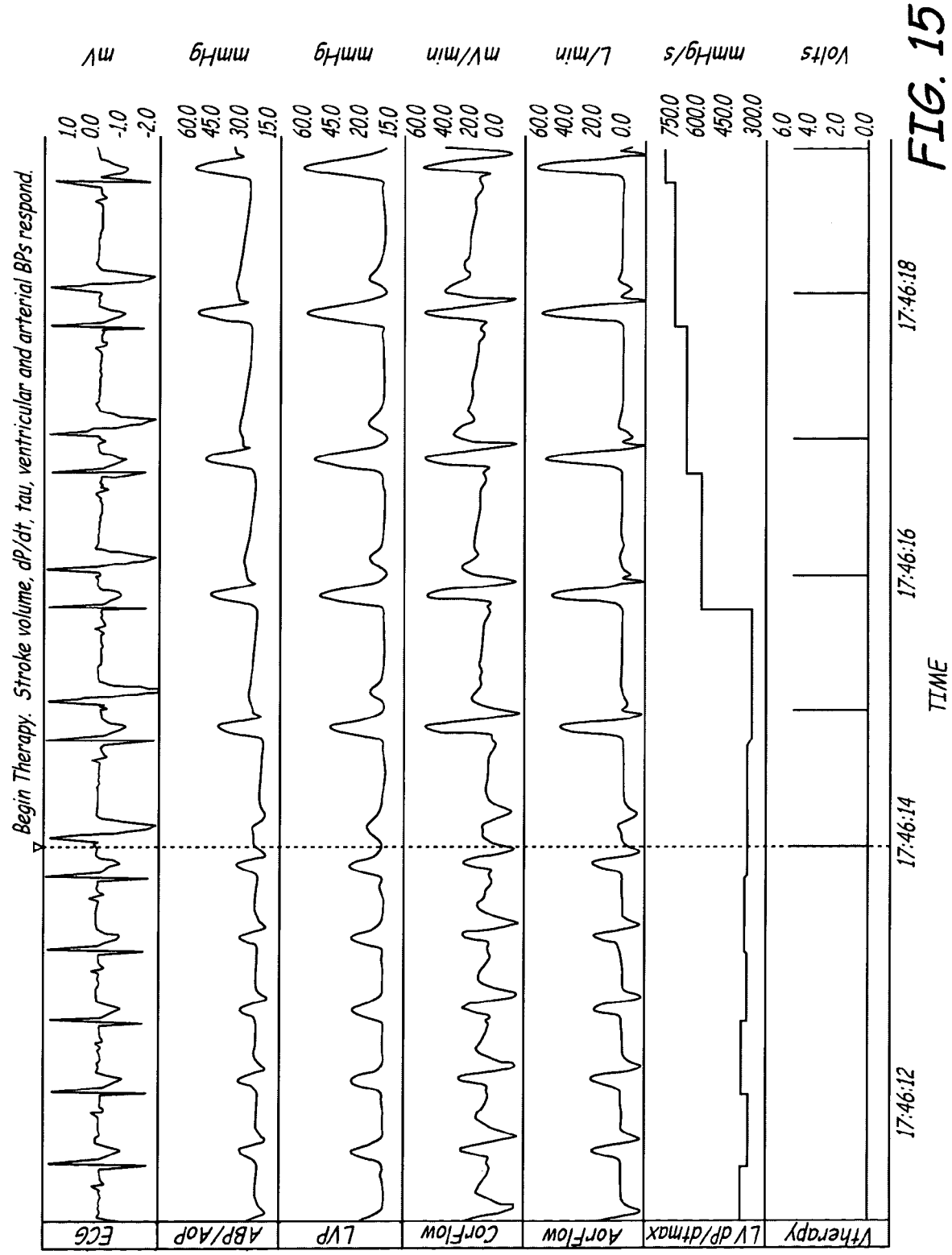
FIG. 15 is a set of traces representing physiologic and therapy activity according to embodiments of the invention.

In FIG. 15, an initiation of and response to PESP stimulation therapy is depicted. In other conditions such as HF, not necessarily associated with a preceding or concurrent tachyarrhythmia, cardiac dysfunction may deteriorate to the point where device initiated therapy is required. The onset of such cardiac dysfunction may either be gradual or sudden but upon establishing sufficient severity and duration, PESP stimulation therapy is begun. The excitatory PESP therapy shown here provides much needed increases of arterial blood pressure (ABP), coronary flow (CorFlow) and aortic flow (AorFlow) and the LV dp/dtmax value more than doubles from pre-PESP therapy in approximately five seconds.

Figure 16:
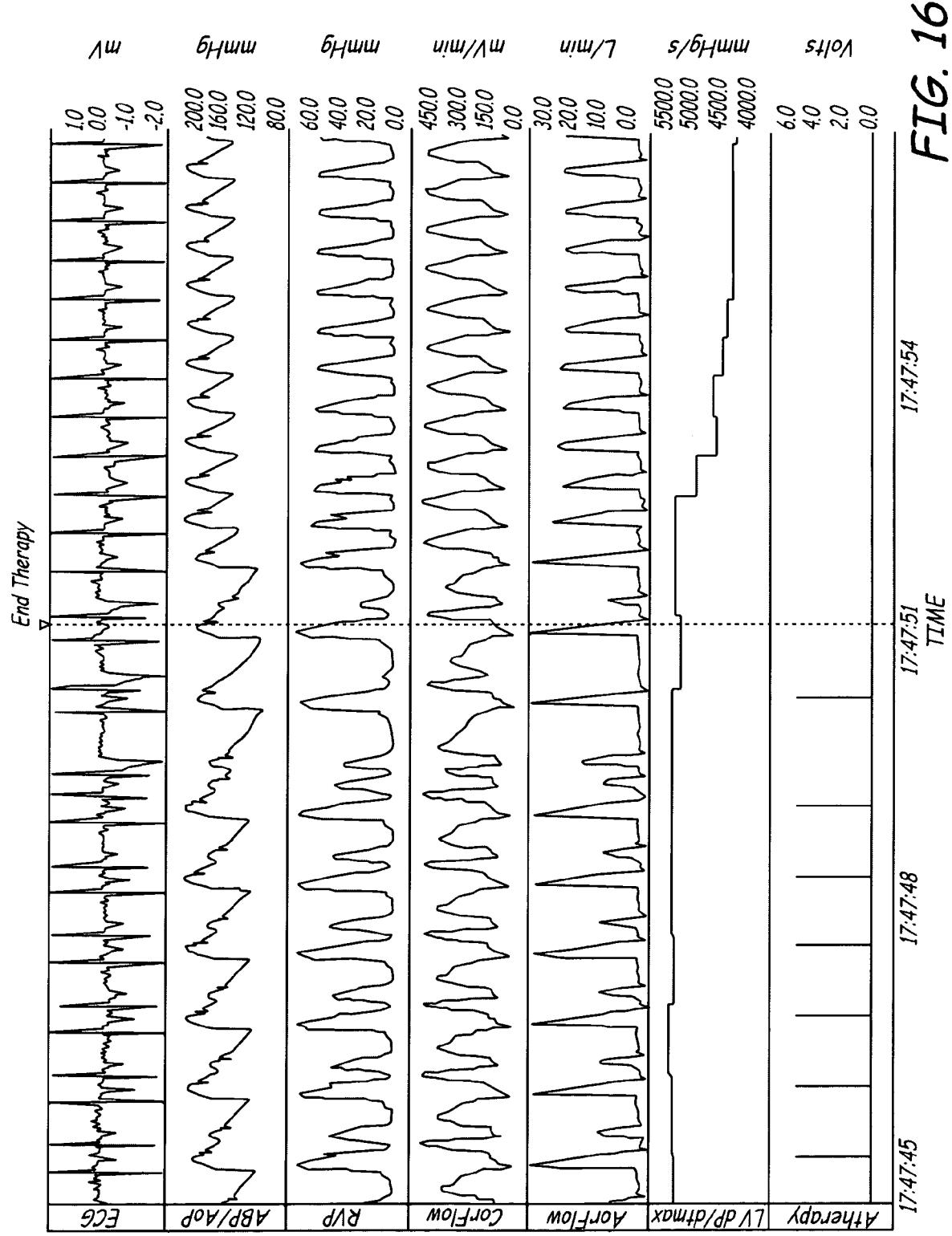
FIG. 16 is a set of traces representing physiologic and therapy activity according to embodiments of the invention.

FIG. 16 depicts termination of PESP therapy based on duration and response criteria. In FIG. 16, the termination criteria are met and PESP stimulation therapy is halted. In this case, stimulation therapy consists of atrial-only PESP stimulation therapy pulses (Atherapy) that capture and reset the sinus node, are conducted to the ventricles, and produce atrial and ventricular PESP due to natural conduction. In this sequence, the patient has maintained a good RV pressure (RVP) and LV dP/dtmax for over 30-60 seconds, and therefore the atrial-only PESP stimulation therapy is halted. Although the heart rate accelerates and contractility diminishes, cardiac function has recovered very significantly from the levels shown in FIG. 14 and FIG. 15 (just described).

Figure 17:
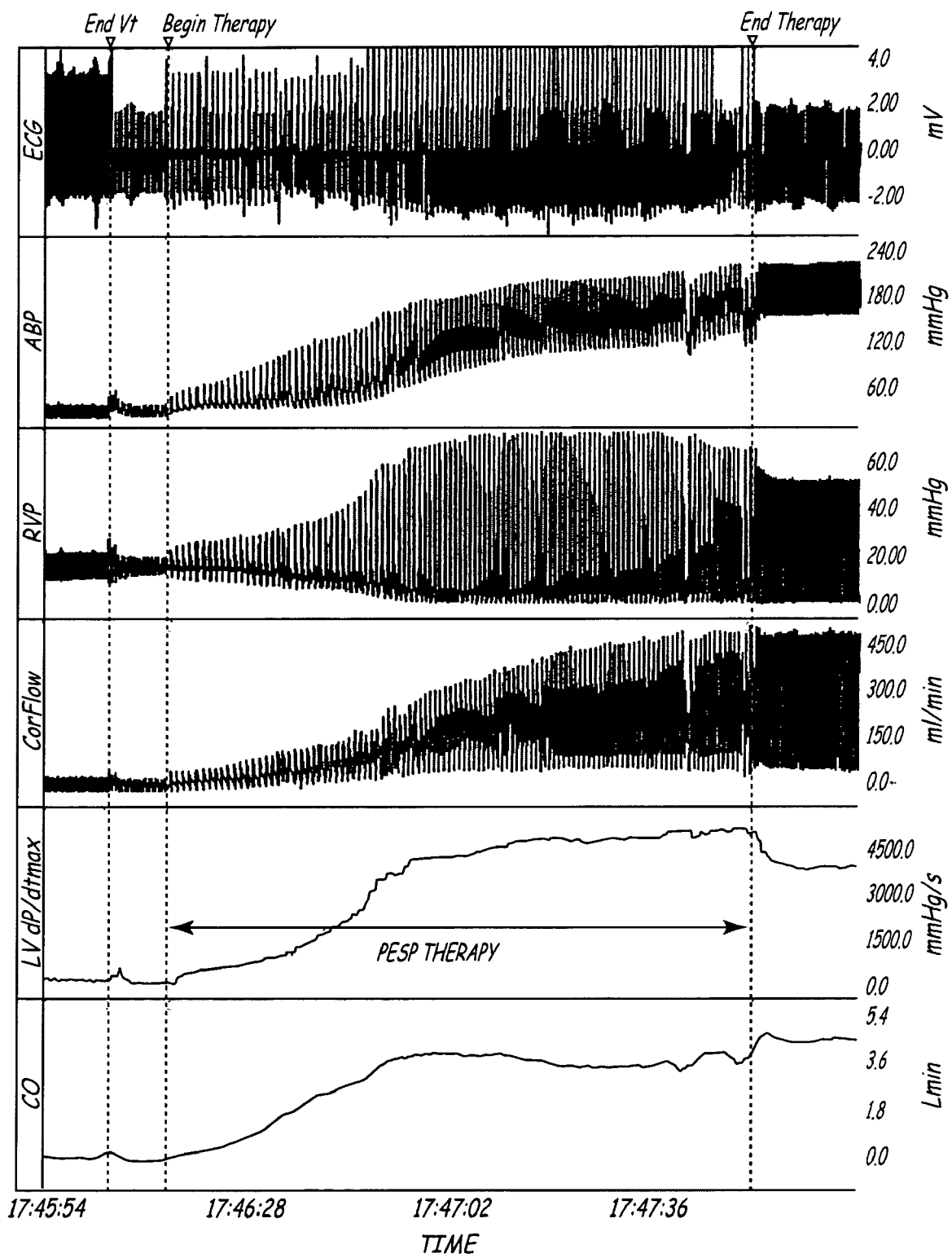
FIG. 17 is a set of traces representing physiologic and therapy activity according to embodiments of the invention.

Now turning to FIG. 17, which depicts a dramatic example of lifesaving PESP stimulation therapy. FIG. 17 illustrates (and clearly demonstrates) that post extra-systolic potentiation stimulation therapy can facilitate rapid recovery of cardiac function following a long duration of paced tachyarrhythmia in an anesthetized canine subject.

In FIG. 17, the trace denoted "ECG" is a surface ECG record, the trace denoted "ABP" is a record of arterial blood pressure measured via a catheter in the aorta of the subject, the trace denoted "RVP" is a record of blood pressure measured within the right ventricle. The trace denoted "CorFlow" is a record of blood flow in the coronary artery, the trace denoted "LVdP/dtmax" is a record of the maximum value of the $1^{st}$ derivative of left ventricular pressure per each cardiac cycle, and the trace denoted "CO" is a recording of cardiac output as derived from mean aortic flow. The record depicted in FIG. 17 begins with the final few seconds of a six-minute long, paced tachyarrhythmia (the portion of the traces before the "End VT" marker). This is followed by approximately 10 seconds of normal sinus rhythm (NSR) with severe hemodynamic dysfunction that could be classified as pulseless electrical activity (PEA) or electro-mechanical dissociation (EMD). During this time, coronary blood flow and cardiac output have not visibly increased compared to flows occurring during the tachyarrhythmia. Without adequate blood flow, the heart will remain ischemic and the subject will likely die of PEA. The portion of FIG. 17 denoted by a horizontal arrow marked "PESP Therapy", marks the period during which PESP pacing therapies were delivered in the right ventricular apex of the heart of the subject. During this period, all measured pressures and flows are appreciably augmented on the very first cardiac cycle following delivery of the first pacing (PESP) stimuli. The values continue to increase and begin to recover to normal physiologic levels within approximately one minute. At the end of the PESP therapy delivery segment, there has been sufficient coronary flow to re-perfuse the heart, allowing it to resume function without additional therapy. It cannot be overemphasized that return of spontaneous circulation in this subject occurred without any pharmacological or mechanical support therapy or treatment but instead relied exclusively on electrical stimulation delivered according to embodiments of the invention.

Figure 18:
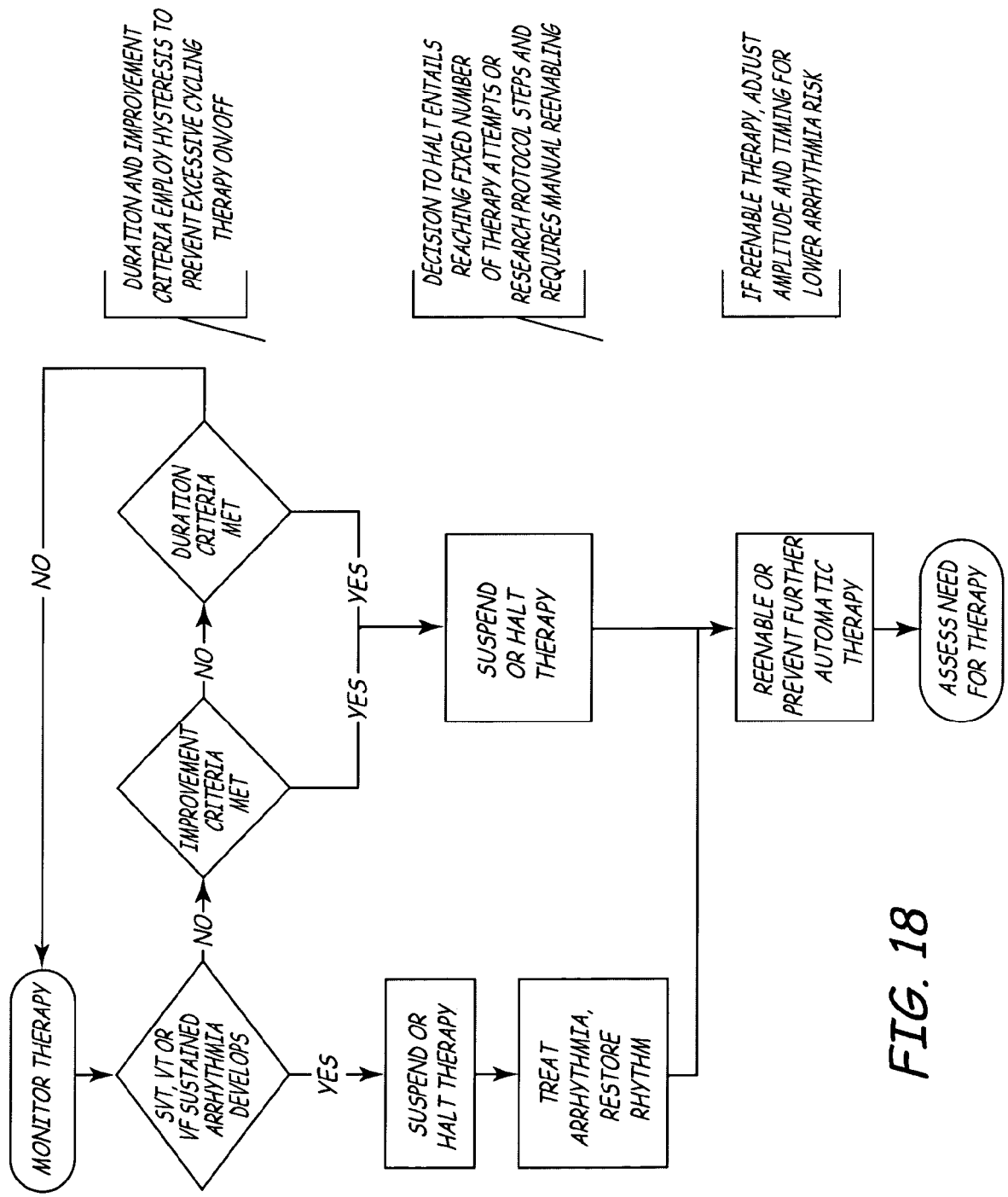
FIG. 18 is a flow chart depicting an additional aspect of embodiments of the invention.

Recognition of the need for such therapy may depend on clinicians or an automated device, either implanted or external, and stimulation therapy applied transcutaneously or from electrodes on or near the heart. FIG. 18, which is an annotated version of FIG. 13, contains some added information regarding duration and improvement criteria, halting therapy delivery and adjustment of amplitude and timing of PESP therapy to lower arrhythmia risk.

The start-stop rules may operate using a variety of schemes and sensor inputs as depicted in FIG. 2 which are microprocessor or hardware controlled and programmable with values determined by algorithms or clinicians, such as depicted in the system diagrams of FIG. 3A and FIG. 3B.

Figure 19:
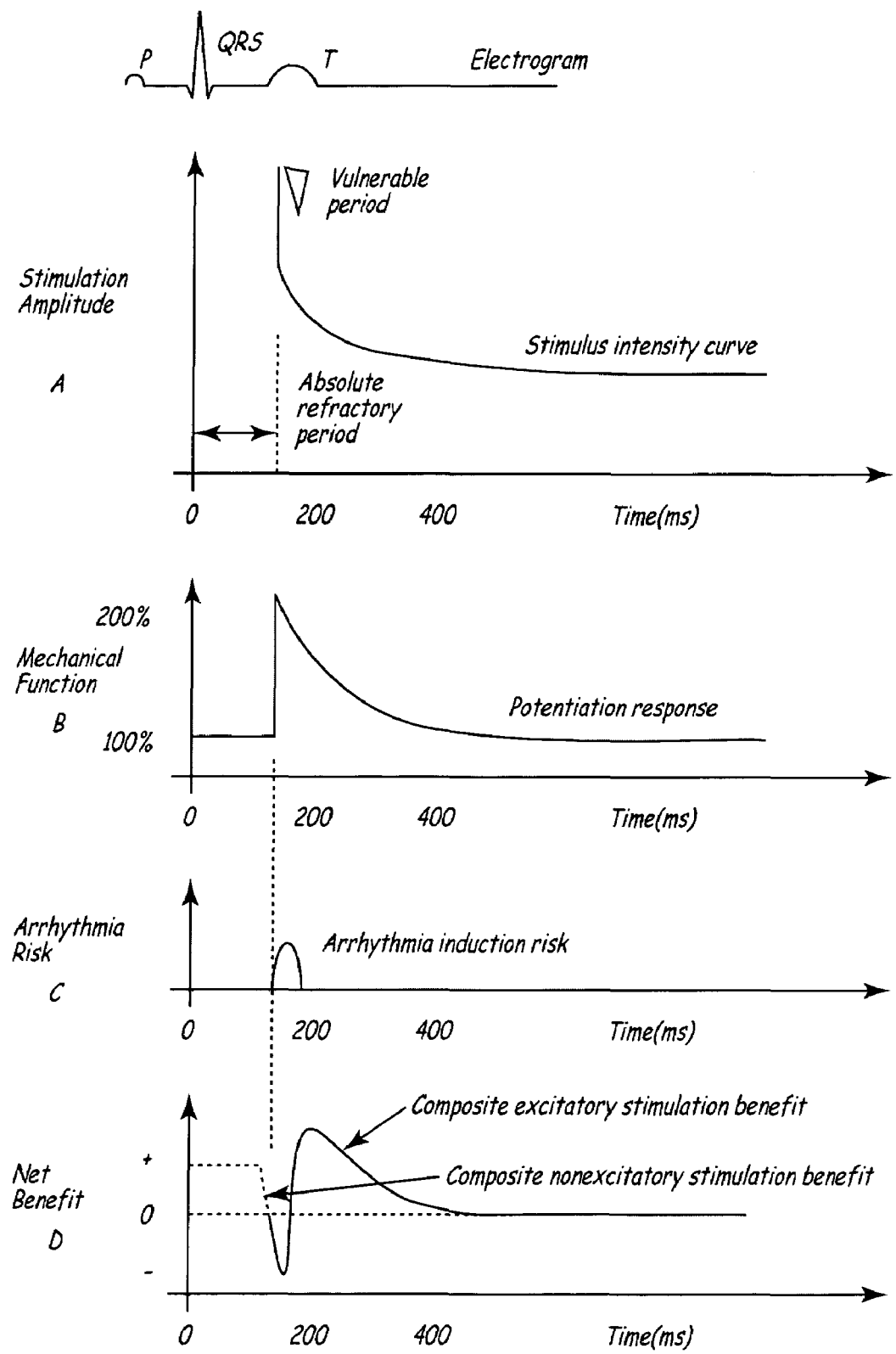
FIG. 19 is a set of four X-Y plots illustrating timing relationships between stimulation amplitude, mechanical function, arrhythmia risk and "net benefit" of therapy delivery according to embodiments of the invention.

Turning now to FIG. 19 (A through D) which is a composite illustration composed of four X-Y plots of data showing critical timing sequences between such plots of data with respect to delivery of excitatory (PESP) and nonexcitatory stimulation (NES) therapy. An unlabeled time-aligned surface representative ECG electrogram trace appears at the top of the figures for ease of cross-reference.

In FIG. 19A, a stimulus intensity curve is depicted wherein a primary determinant of the timing associated with arrhythmia risk and hemodynamic benefit derived from PESP excitatory stimulation. It will be appreciated that stimulation pulses of greater amplitude than the curve (at a given moment in time) are necessary to capture and thus provide benefit from PESP stimulation therapy. An absolute refractory period is depicted in FIG. 19A. During this period no depolarizations result and this period is ideal for applying (NES) with electrodes near the heart. In the period labeled "vulnerable period", which occurs just outside of the absolute refractory period, very high amplitude pulses can cause arrhythmias including repetitive extrasystoles, VT, or VF. For practical purposes, excitatory stimulation pulses are delivered some margin above the threshold so that capture is maintained. Stimulation pulse amplitude, however, is also maintained low so that the risk of arrhythmias is very low even when timed to coincide with the vulnerable period (for comparison see FIG. 19C, "arrhythmia induction risk curve"). As is well known in the literature, the magnitude of the potentiation seen on the beat following the extrasystole (the post extrasystole beat) is a function of the extrasystole's timing—becoming greatest at the shortest interval resulting in capture (as shown in FIG. 19B, labeled "potentiation response" curve). The solid curve depicted in FIG. 19D (labeled "Net Benefit" curve), combines physiologic benefit from both NES and PESP stimulation and arrhythmia risk. It is not desirable to apply a PESP stimulation immediately after the absolute refractory boundary. The dashed Net Benefit curve shows that NES is best delivered during the refractory period, or else excitation and/or arrhythmia could result. Embodiments of the invention include methods to help the clinician or automated device determine the refractory/nonrefractory boundary and thus achieve the benefits of the intended therapies while controlling risk.

Figure 20:
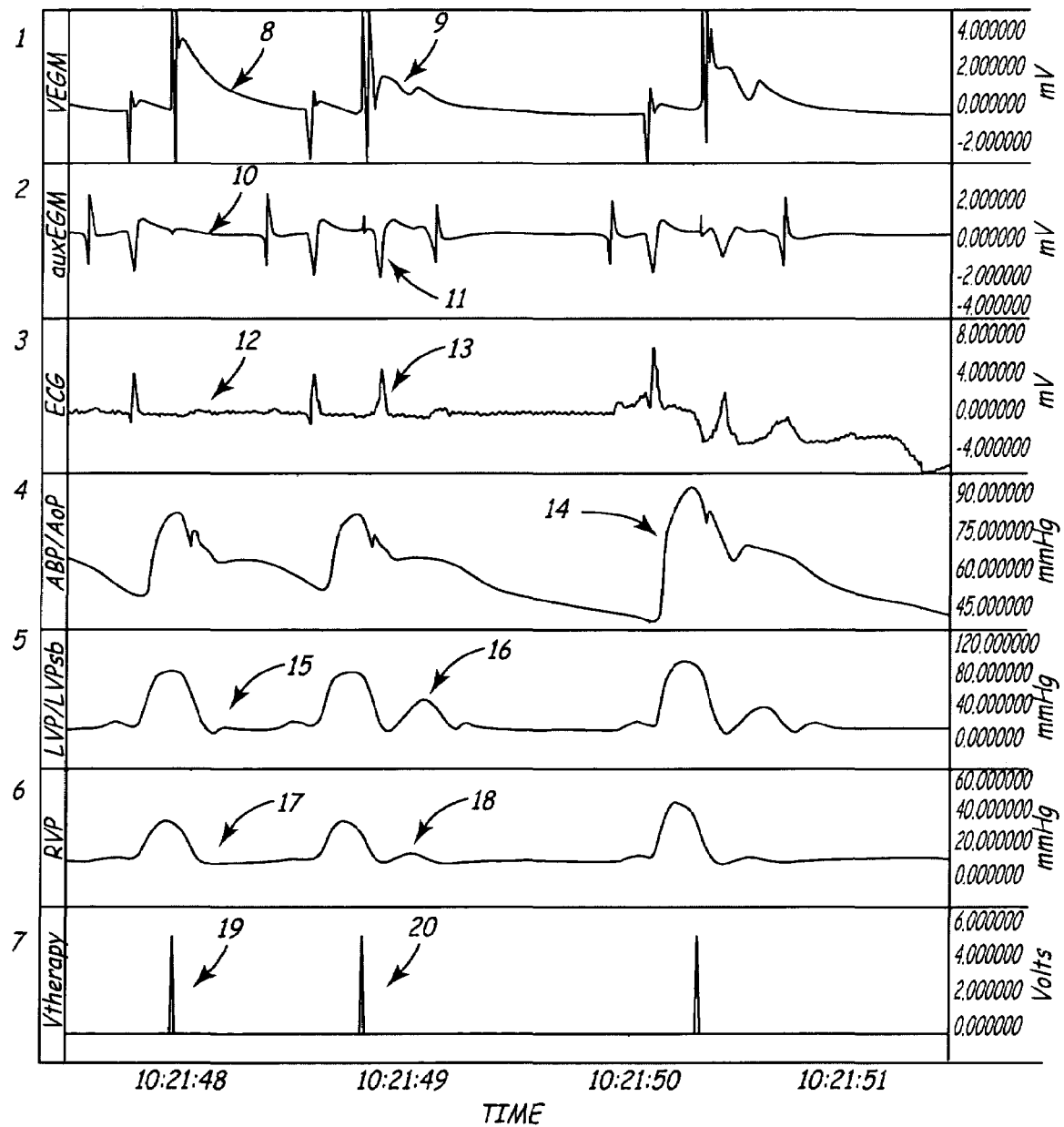
FIG. 20 is a set of traces representing physiologic and therapy activity according to embodiments of the invention.

Referring now to FIG. 20, which is a graphical depiction of electrical and hemodynamic detection of cardiac chamber capture. The trace labeled "1" is a ventricular electrogram (VEGM) obtained from the site of application of the stimulation therapy. The trace labeled "2" is a second electrogram that is near both right atrium and right ventricle and is away from the site of application of the pacing therapy. The trace labeled "3" is a surface ECG, traced "4" is a record of arterial blood pressure (ABP), trace "5" is a record of left ventricular pressure (LVP), trace "6" is a record of right ventricular pressure (RVP) and trace "7" is a marker channel record of stimulation therapies applied to the ventricles (Vtherapy). FIG. 20 illustrates embodiments of the concept of the identification of whether or not a cardiac potentiation therapy lays inside or outside the cardiac refractory period.

With respect trace 7, arrow 19 identifies a therapy is delivered to the ventricle that lies inside the refractory period; arrow 20 identifies a therapy that lies outside the refractory period. With respect to trace 1, arrow 8 identifies an electrogram tracing following a therapy that shows no evidence of a resultant depolarization, confirming that the therapy lies in the refractory period, and arrow 9 identifies an electrogram tracing showing a cardiac depolarization following the therapy, confirming that the therapy pulse, had sufficient amplitude and duration, was outside the refractory period, and captured the myocardium.

Similarly, with respect to trace 2, arrows 10 and 11 identify noncapture and capture, respectively, from the electrogram at an auxiliary electrode site suitable to identify pulses inside and outside of the cardiac refractory period by the absence or presence of a ventricular depolarization. With respect to trace 3, arrows 12 and 13 identify the absence and presence of ventricular depolarizations on a surface ECG, respectively.

An embodiment of embodiments of the invention would be to apply a detection algorithm to electrogram signals (possibly including but not limited to signal traces 1-3) and identifying the presence or absence of an evoked depolarization. This information is then used to identify whether the preceding therapy was inside or outside of the cardiac refractory period.

With respect to trace 4, arrow 14 points to a significantly augmented ABP wherein the arterial pulse pressure was augmented on the cardiac cycle following a therapy that lies outside the refractory period. Similarly, LVP (trace 5) and RVP (trace 6) are also augmented on the cycle following capture. Thus, FIG. 20 illustrates an embodiment of embodiments of the invention used to detect the presence of pressure, flow, acceleration, impedance change, or other favorable evidence of mechanical augmentation following therapy delivery. This evidence also helps identify whether or not the preceding therapy was delivered inside or outside of the cardiac refractory period.

With respect to traces 5 and 6, arrows 15 and 17 indicate portions of a left and right ventricular pressure waveform, respectively, resulting from stimulation therapy delivered in the cardiac refractory period. As a result, no evidence of an extra-systole is seen following the therapy.

Again with respect to traces 5 and 6, arrows 16 and 18 are pressure waveforms following a therapy delivered outside of the cardiac refractory period. A small increase in pressure can be seen, associated with the extra-systole following therapy delivery outside the refractory period. Another embodiment of embodiments of the invention is adapted to apply a detection algorithm to a sensor that makes a measurement of cardiac mechanical activity, including but not limited to right ventricular, left ventricular or arterial pressure, dimension, or acceleration and identifying the presence or absence of an extra systole. This information is used to identify whether the preceding therapy was inside or outside of the cardiac refractory period. Evoked R wave detection information may then be used to time or trigger delivery of a stimulation therapy that would cause post extra-systolic potentiation or would be nonexcitatory for NES, or both.

Figure 21:
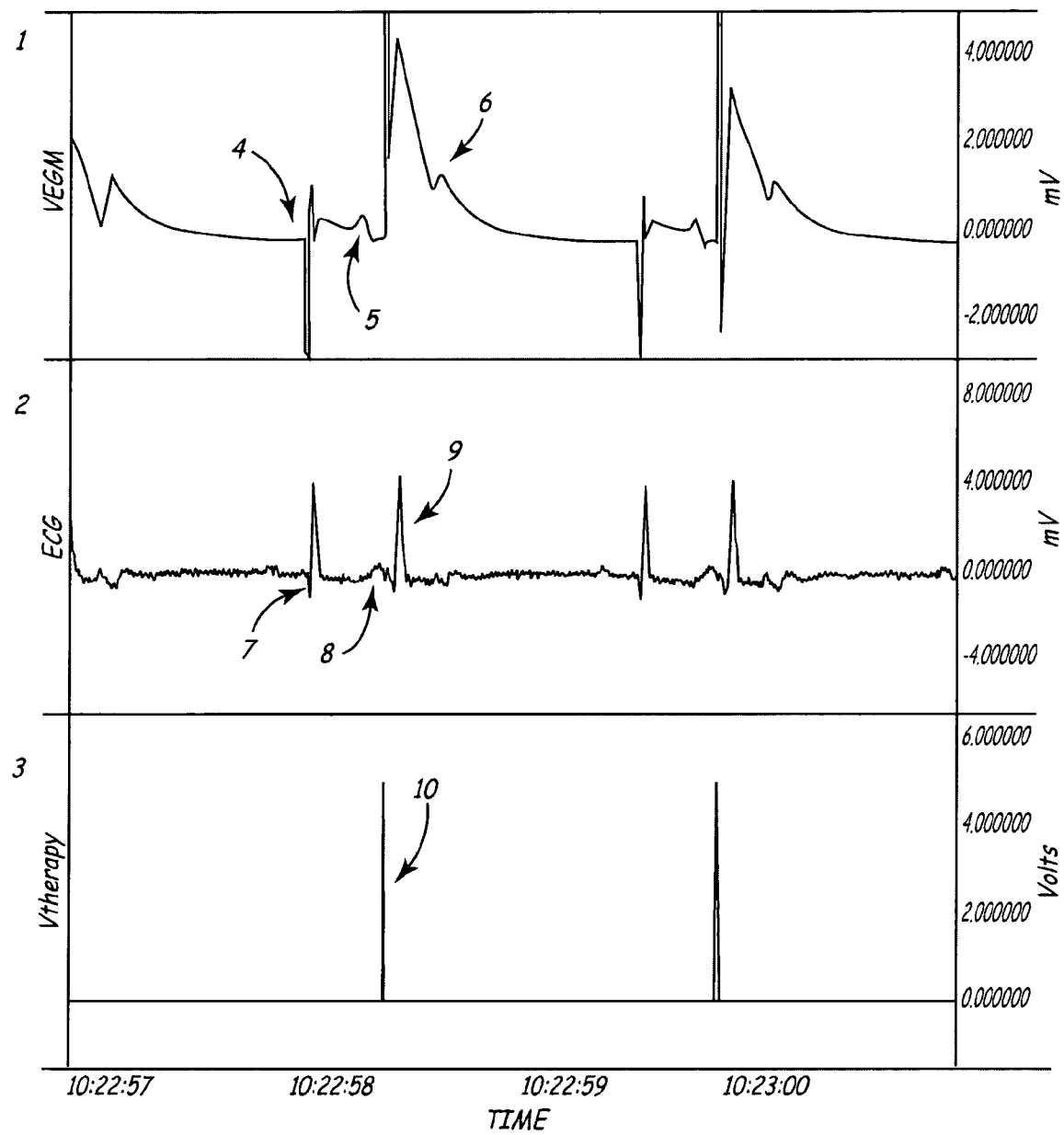
FIG. 21 is a set of traces representing physiologic and therapy activity according to embodiments of the invention.

FIG. 21 depicts three traces, VEGM, ECG and Vtherapy, respectively which can be used to determine whether or not capture has occurred by analyzing a T wave. Trace 1 is a ventricular electrogram (VEGM) from the site of application of the stimulation therapy, trace 2 is a surface ECG, and trace 3 is a marker channel record of applied stimulation therapies. With respect to trace 1 and 2, arrows 4 and 7 are electrogram signals indicating a ventricular depolarization and arrows 5 and 8 are signals showing a resulting ventricular repolarization or T-wave. In trace 3, arrow 10 corresponds to a marker of the delivered therapy, which was applied just after the T-wave. In trace 2, arrow 9 is an evoked ventricular depolarization. In trace 1, arrow 6 is an evoked T resulting from repolarization.

Another embodiment of the therapy capture aspect of these teachings is used to identify the evoked T-wave from an electrogram signal following application of a therapy pulse. A further embodiment is to rely directly on the time of occurrence of the T-wave (between the depolarization and repolarization from an electrogram signal) to form an index of the boundary between refractory (before the T-wave) and nonrefractory (after the T-wave) intervals. The T-wave detection information may then be used to time or trigger delivery of a stimulation therapy that would cause post extra-systolic potentiation (delivered after the refractory period) or would be nonexcitatory for NES (delivered during the refractory period to cardiac tissue or at any point to nerves not near cardiac tissue), or both.

Figure 22A:
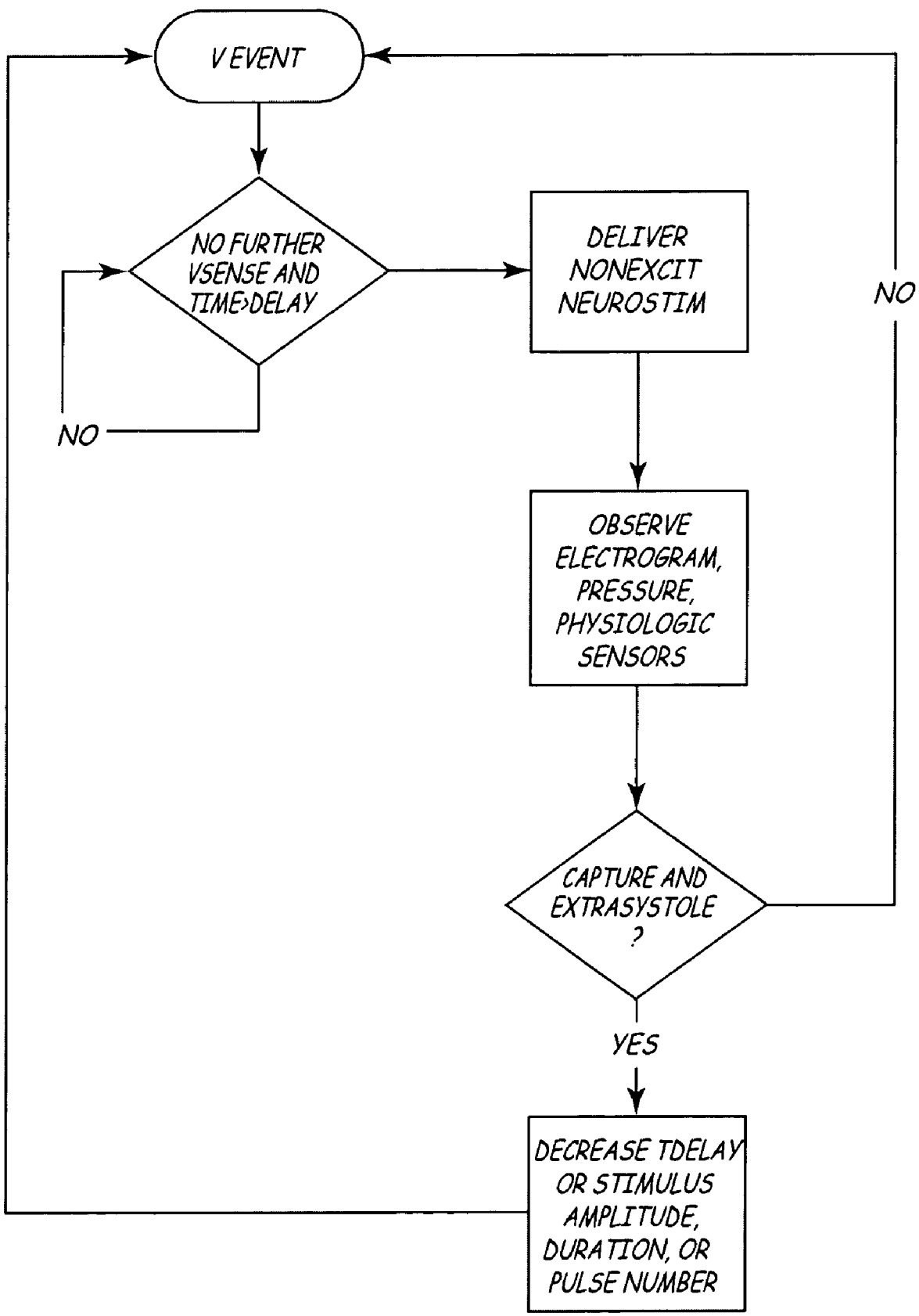
FIG. 22A is a flow chart depicting an additional aspect of embodiments of the invention.

FIG. 22A is a flow chart that diagrams response to capture information to apply (NES) therapy alone. Following a ventricular pace or sense event, the sensing circuits remain active and a timer counts down a delay until the scheduled delivery of the NES pulse(s). If there has been no intrinsic event in this interval, the NES pulse(s) are delivered and electrogram or mechanical sensor signals employed (such as described herein above) to determine if capture and/or an extrasystole occurred. If capture did occur, the delivery time, stimulation amplitude, or pulse number is decreased and the process repeated. The value for ESI (here referred to as Tdelay) is typically 200-300 ms. Tdelay and other stimulus parameters may also be influenced by observations of heart rate or other physiologic sensors in addition to the electrical and mechanical parameters discussed above.

Figure 22B:
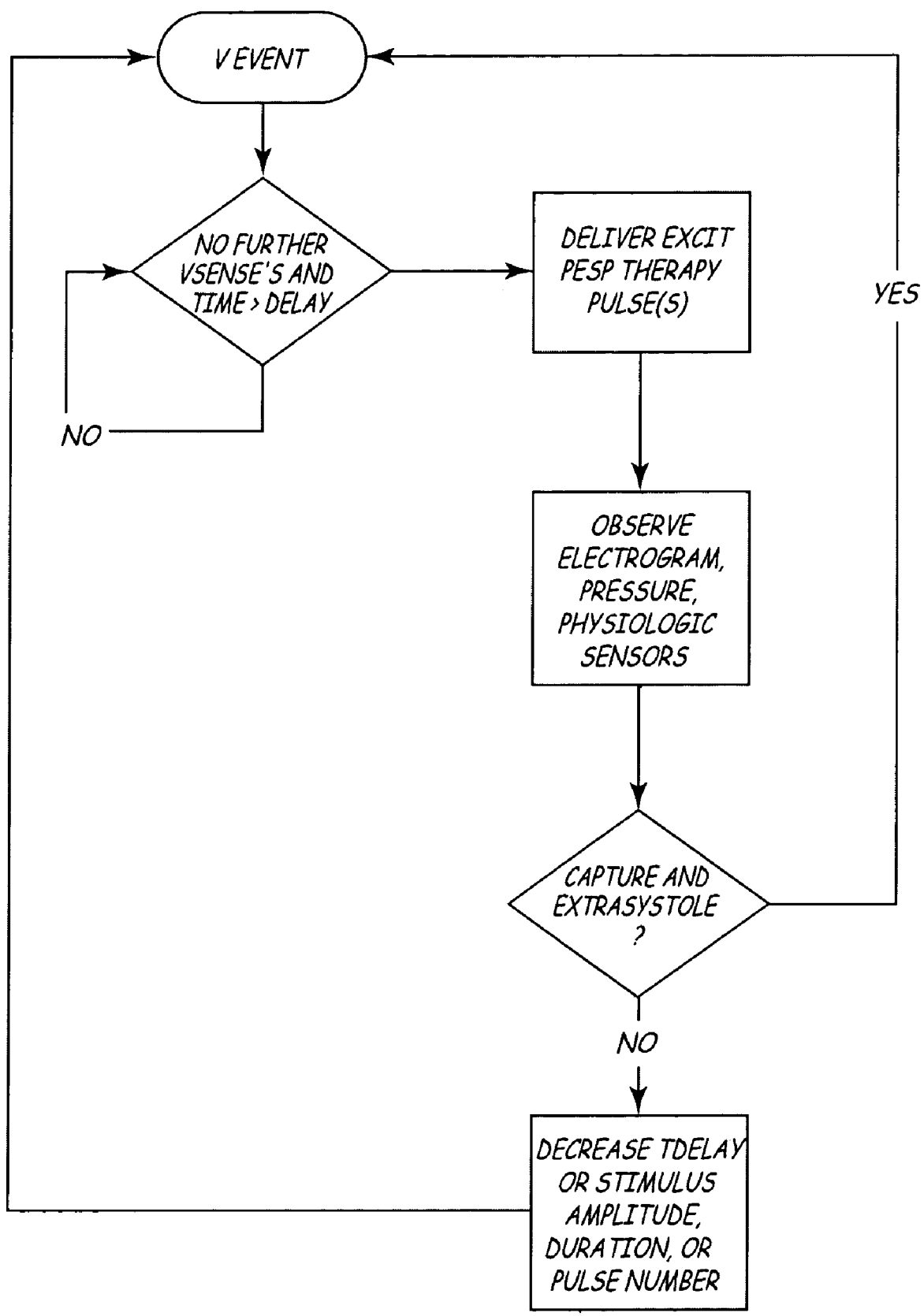
FIG. 22B is a flow chart depicting an additional aspect of embodiments of the invention.

FIG. 22B is a flow chart that diagrams response to capture information to apply excitatory PESP therapy. Following a ventricular pace or sense event, the sensing circuits such as depicted in FIG. 3A and FIG. 3B remain active and a timer counts down a delay until the scheduled delivery of the PESP stimulation pulse(s). If there has been no intrinsic event in this interval, the pulse(s) are delivered and electrogram or mechanical sensor signals employed (such as described herein above) to determine if capture and/or an extrasystole occurred. If capture did not occur, the therapy delay, delivery time, stimulation amplitude, or pulse number is decreased and the process repeated. The value for Tdelay is typically 200-300 ms. Tdelay and other stimulus parameters may also be influenced by observations of heart rate or other physiologic sensors in addition to the electrical and mechanical parameters discussed above. This algorithm is also used for the pulse(s) intended to produce PESP when accompanied by NES pulse(s).

Figure 23:
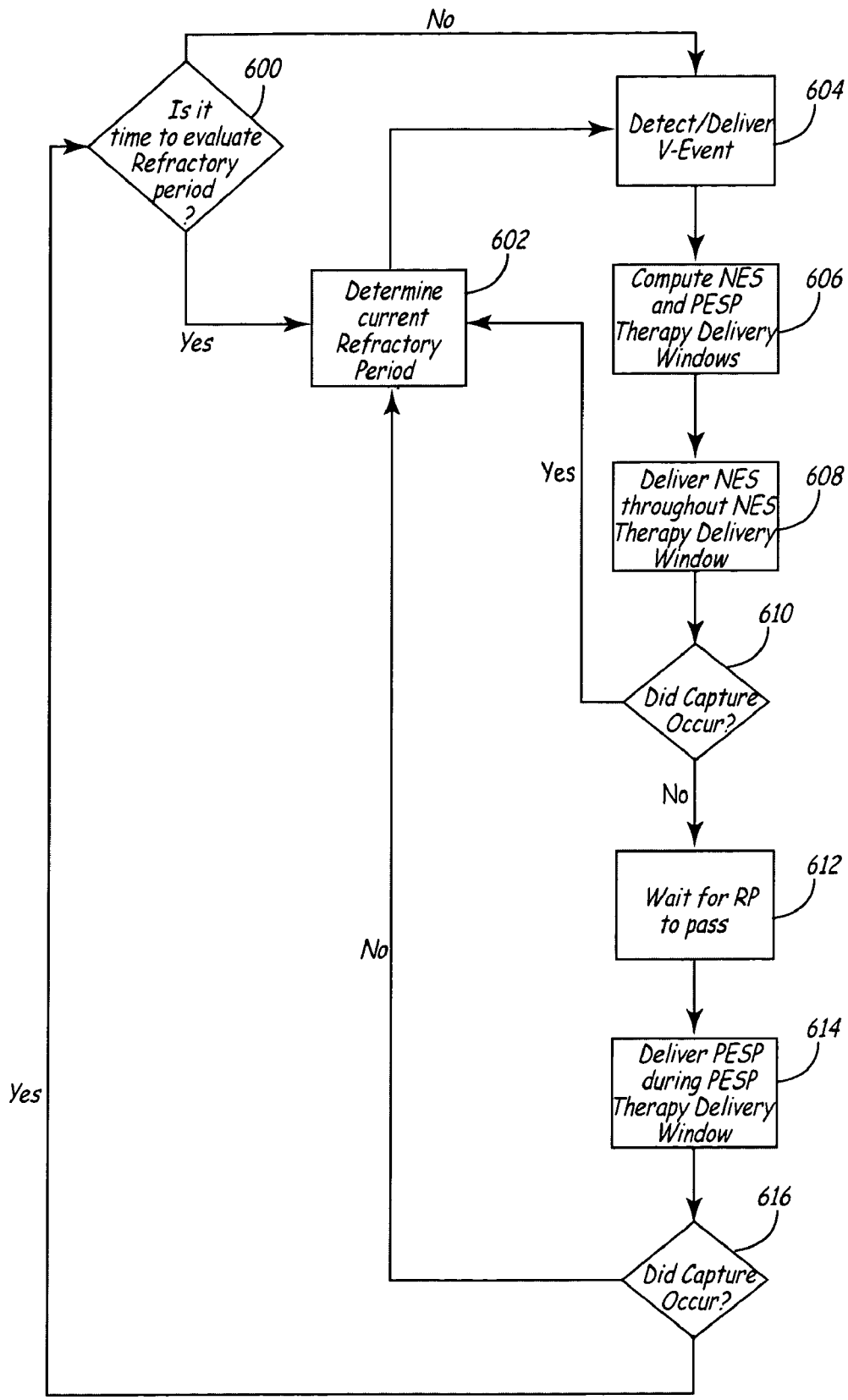
FIG. 23 is a flow chart depicting an additional aspect for determining when to deliver NES and when to deliver PESP therapies in an embodiment of the invention.

FIG. 23 is a flow chart depicting an additional aspect for determining when to deliver NES and when to deliver PESP therapies in an embodiment of the invention. At state 600 IMD 14 determines whether it is time to evaluate the refractory period (RP). If it is time to evaluate the RP, IMD 14 then determines the current RP at state 602. If it is not time to evaluate the RP, IMD 14 proceeds to state 604 to either detect an intrinsic ventricular pulse or deliver a pace to ventricle. IMD 14 also proceeds to state 604 after the RP is determined. At state 606 IMD 14 computes the NES and PESP therapy delivery windows. IMD 14 can then deliver an NES therapy throughout the NES therapy delivery window at state 608 if NES therapy is needed. IMD 14 will then determine if capture has occurred at state 610. If capture has occurred, IMD 14 returns to state 602 to determine the current RP. If capture did not occur, IMD 14 proceeds to state 612 and waits for the RP to pass. After the RP has passed PESP therapy can then be delivered in the PESP therapy delivery window at state 614 if PESP therapy is needed. IMD 14 then again determines if capture has occurred at state 616. If capture has not occurred, IMD 14 returns to state 602 to determine the current RP. If capture did occur, IMD 14 proceeds to state 600 to evaluate the RP.

The identification of refractory and non-refractory intervals and appropriate timing of pulses may operate using a variety of timing schemes and sensing circuits which are both preferably microprocessor or hardware controlled and programmable with input values determined by algorithms or clinicians, such as depicted in the system diagrams of FIG. 3A and FIG. 3B.

Figure 24:
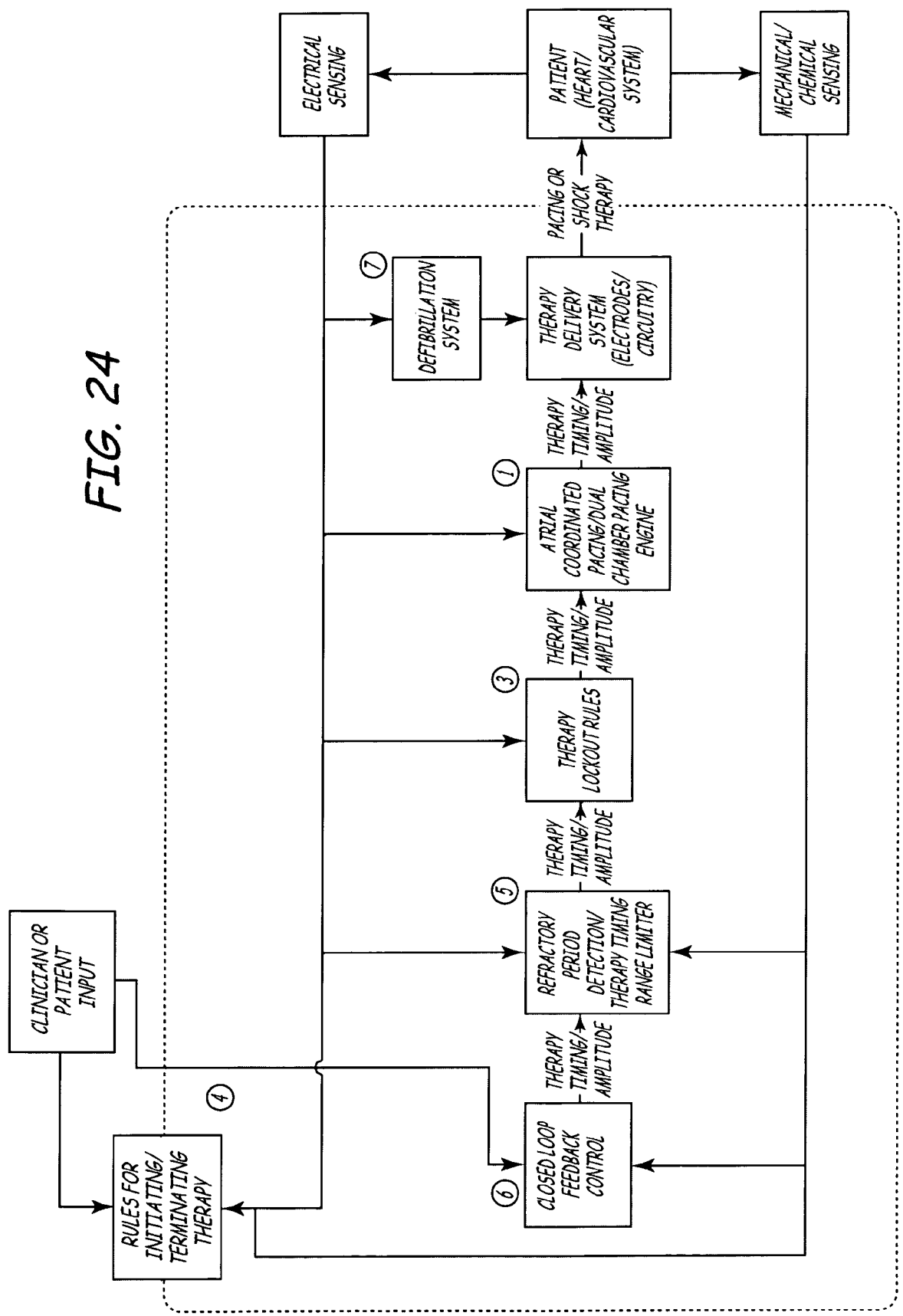
FIG. 24 is a flow chart depicting an additional aspect of embodiments of the invention.

FIG. 24 is a flowchart illustrating significant aspects of stimulation therapies according to some aspects of embodiments of the invention described herein. Various components of these teachings work together to provide safe and effective stimulation therapies for cardiac dysfunction, including arrhythmias and HF, among others. Beginning with the upper left portion of FIG. 24, block 4 incorporates the rules by which therapy as a whole is initiated or terminated, thus this aspect (block 4) encloses the others in the dotted border. This aspect may be an automated algorithm or may require input from a clinician or the patient. Block 6 depicts the closed loop feedback controller that gathers a measure of cardiac function from the mechanical sensors and a desired control point from the clinician or patient. The controller depicted as block 6 then adjusts the timing or the amplitude of the therapy to achieve this desired control point. Block 5 includes the algorithms used to identify the refractory period of the heart that uses as an input either electrical sensing of cardiac depolarizations or repolarizations or mechanical sensing of extra-systoles or potentiation. If NES is desired, the algorithm keeps the therapy timing within the refractory period. In the case of PESP stimulation, the therapy timing falls outside the refractory period. Block 5 can also be viewed as a range limiting system; it limits the range of therapy timings that it receives from the feedback controller. Block 3 includes the algorithms that lock out therapy if an abnormal cardiac event such as a premature ventricular contraction or a tachyarrhythmia occurs. Block 1 is the dual-chamber pacing engine of the device, incorporating full dual chamber sensing/pacing capability with the added functionality of atrial coordinated pacing (ACP) with PESP therapies. Finally, block 7 is a defibrillation system including detection of tachyarrhythmic events and application of either shock or pacing therapies such as ATP to terminate these events. The system also includes new rules to increase survivability of long duration episodes of tachycardia or dysfunction normally associated with high-mortality.

While the various components depicted in FIG. 24 preferably are integrated into a single medical device not all such components must be included in any particular medical device. In fact, the components may be distributed between remote devices and coupled wirelessly or otherwise to perform according to the foregoing description. Medical devices employing such components may comprise IMDs, AED or other external medical devices, device programmers, temporary pacing/defibrillation devices and the like.

As discussed above, PESP is an effective therapy for providing improved cardiac function in patients with heart failure or patients who are in a post-shock depressed cardiac state. It is thought that PESP works through an increase in calcium loading of the sarcoplasmic reticulum (SR) from intracellular calcium. It is accomplished through a premature electrical depolarization of the myocardial cells without causing the SR to release its calcium stores as it normally would. Advantageously, the SR is allowed to continue to load calcium from the intracellular space, thus resulting in more calcium in the SR for the next PESP pulse. As an analogy, the SR can be thought of as the pump and PESP can be thought of as priming the pump.

Similarly, NES pacing enhances cardiac performance through the application of electrical current during the refractory period to modify calcium handling in the cell. It is thought that the effects of NES pacing may be a result of increased calcium loading into the intracellular space through L-type calcium ion channels in the cell membrane, making more calcium available for contraction, thereby enhancing contractility. Extending the analogy of the SR as a pump, the NES pacing can be thought of as increasing the available reservoir for the pump. Therefore, while both PESP and NES enhance cardiac performance through modulation of calcium handling within myocardial cells, there are fundamental differences in which parts of the calcium handling cycle is modified for the two therapies.

In an embodiment of the invention, PESP and NES, which by themselves are helpful for patients with heart failure, are combined in various ways to provide an even greater and more effective therapy. Combining these therapies takes advantage of the two different mechanisms at the core of how these therapies work by altering the manner in which calcium is released for excitation contraction coupling. There may be instances where one type of therapy may make more physiologic sense and other instances where the other therapy may be more beneficial. There may also be other instances where the two therapies may be used together to provide a further boost in cardiac performance. As will be described below, there are potential scenarios of how these therapies could be used together and methods for dynamically turning either or both on and off to meet the unique needs of the patient.

Figure 25:
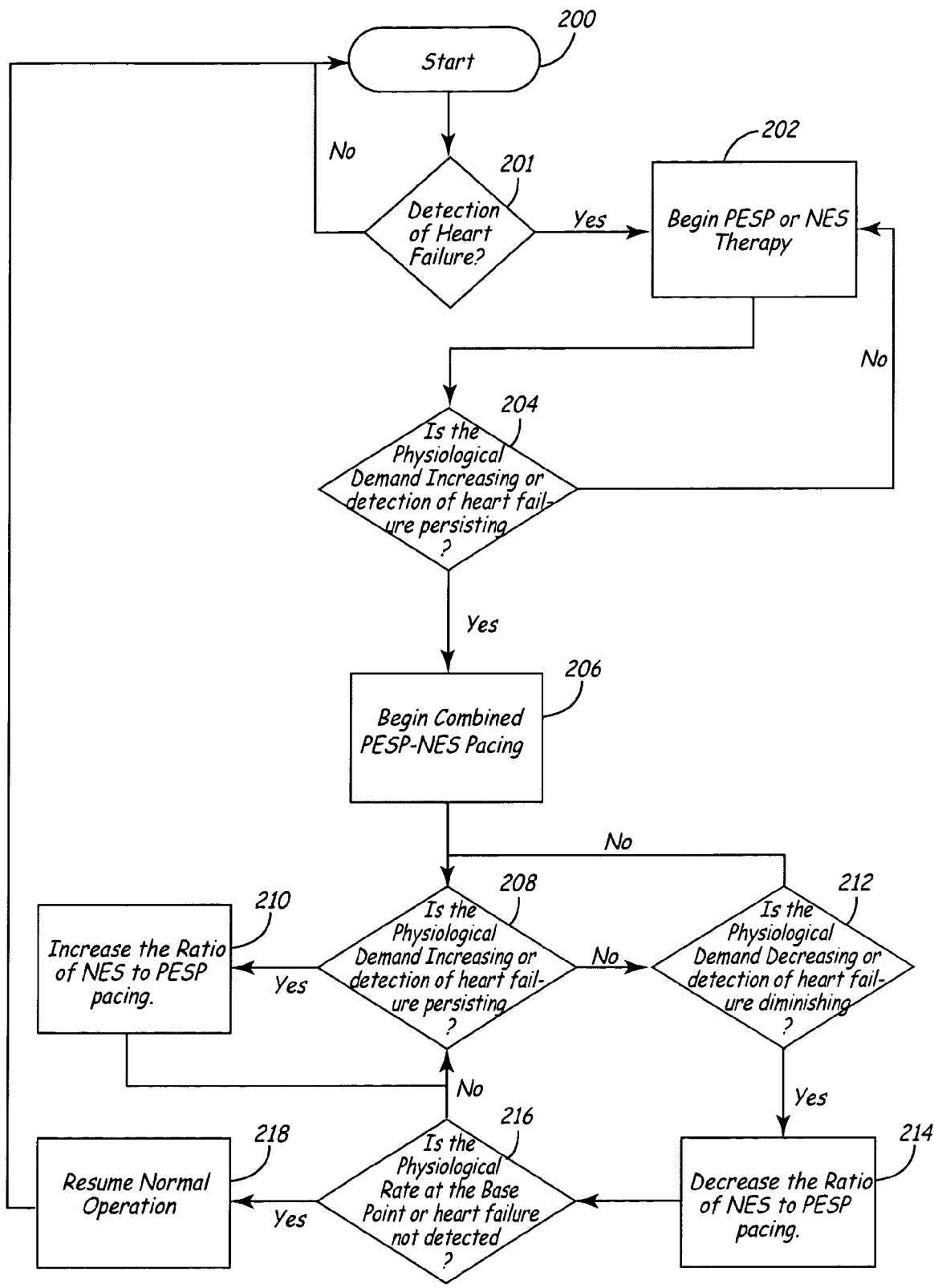
FIG. 25 is a flowchart diagram showing a method of combination PESP/NES pacing based upon physiologic demand in an embodiment of the present invention.

With reference to FIG. 25, a flowchart diagram shows a method of combination PESP/NES pacing based upon physiologic demand in an embodiment of the present invention. In the embodiment of FIG. 25, IMD 100 provides a pacing therapy that switches between various modes based upon physiologic demand. This demand could be determined by heart rate, exercise (accelerometer), breathing rate (minute ventilation), ventricular or vascular pressures (or dP/dt's), oxygen saturation, $pCO_2$, $PO_2$, or any other variables of physiologic demand measurable by IMD 100. Demand is meant as a general term to cover the body as a whole, but could include cardiac specific parameters such as patient activity, breathing patterns, as well as heart rate, cardiac pressures, acceleration, etc. At low physiologic demand, IMD 100 may operate in a PESP only mode. At medium physiologic demand, IMD 100 may switch to PESP pacing on every heartbeat and NES pacing applied every N of M heartbeat (where N is most likely between 2 and 10). At a high physiologic demand, IMD 100 may apply both PESP and NES pacing on every beat to insure maximum contractility and hemodynamics. It is also contemplated IMD 100 could have a more graded adjustment of both therapies without departing from the spirit of the invention.

At state 200, IMD 100 will be in a normal operation set with a base heart rate typically programmed during implantation. Each heart rate indicates what the patient's heart should be when the patient is resting or at a very low physiologic demand. At the base rate the patient may be utilizing a pacing therapy or may be utilizing no pacing therapy at all. IMD 100 will be continuously monitoring the patient for heart failure indicators at state 201. If heart failure is not detected, IMD 100 returns to state 200. Upon detection of a heart failure indicator, IMD 100 begins a PESP or NES therapy to improve hemodynamics at state 202. At state 204, IMD 100 determines the patient's physiologic status and determines whether the physiologic demand is increasing, thus indicating a greater demand on the heart. If there is no increased demand, IMD 100 resumes operation at state 202. If there is an increased demand, the current pacing therapy is mode switched to implement a combined PESP NES pacing therapy at state 206. As stated above, at low physiologic demand, IMD 100 may operate in a PESP or NES only mode and at medium physiologic demand, IMD 100 may switch to PESP pacing on every heartbeat and NES pacing applied every N of M heartbeat where N decreases in number as the physiologic demand increases. By efficiently utilizing NES pacing, IMD 100 is able to conserve battery power, as NES pacing requires significantly more energy than PESP pacing. At state 208, IMD 100 is still continuously monitoring the physiologic demand. If the physiologic demand is still increasing, IMD 100 can then increase the frequency of the NES pacing at state 210 until a pace is applied every heartbeat at the highest physiologic demand. IMD 100 also continues to monitor the physiologic demand at state 208.

If the physiologic demand is no longer increasing, IMD 100 then inquires as to whether the physiologic demand is decreasing at state 212. If the physiologic demand is not decreasing, then IMD 100 returns to state 208 to determine if the physiologic rate is instead increasing. If the physiologic demand is decreasing, then IMD 100 can decrease the ratio of NES to PESP pacing at state 214. For example, IMD 100 could increase the number for N, thus increasing the time between NES pacing pulses. IMD 100 can then determine if the patient's physiologic demand has returned to its baseline physiologic state 216. If the patient's physiologic demand has not returned to its baseline physiologic state (could be rate or other physiologic condition), IMD 100 continues to monitor physiologic demand at state 208. If the patient's physiologic demand has returned to the baseline physiologic state, IMD 100 can then resume operation at state 200.

It is of note that the PESP and NES therapy could occur at the same location in the heart or could occur at opposite locations. Further, both therapies could occur in multiple locations without departing from the spirit of the invention.

Figure 26:
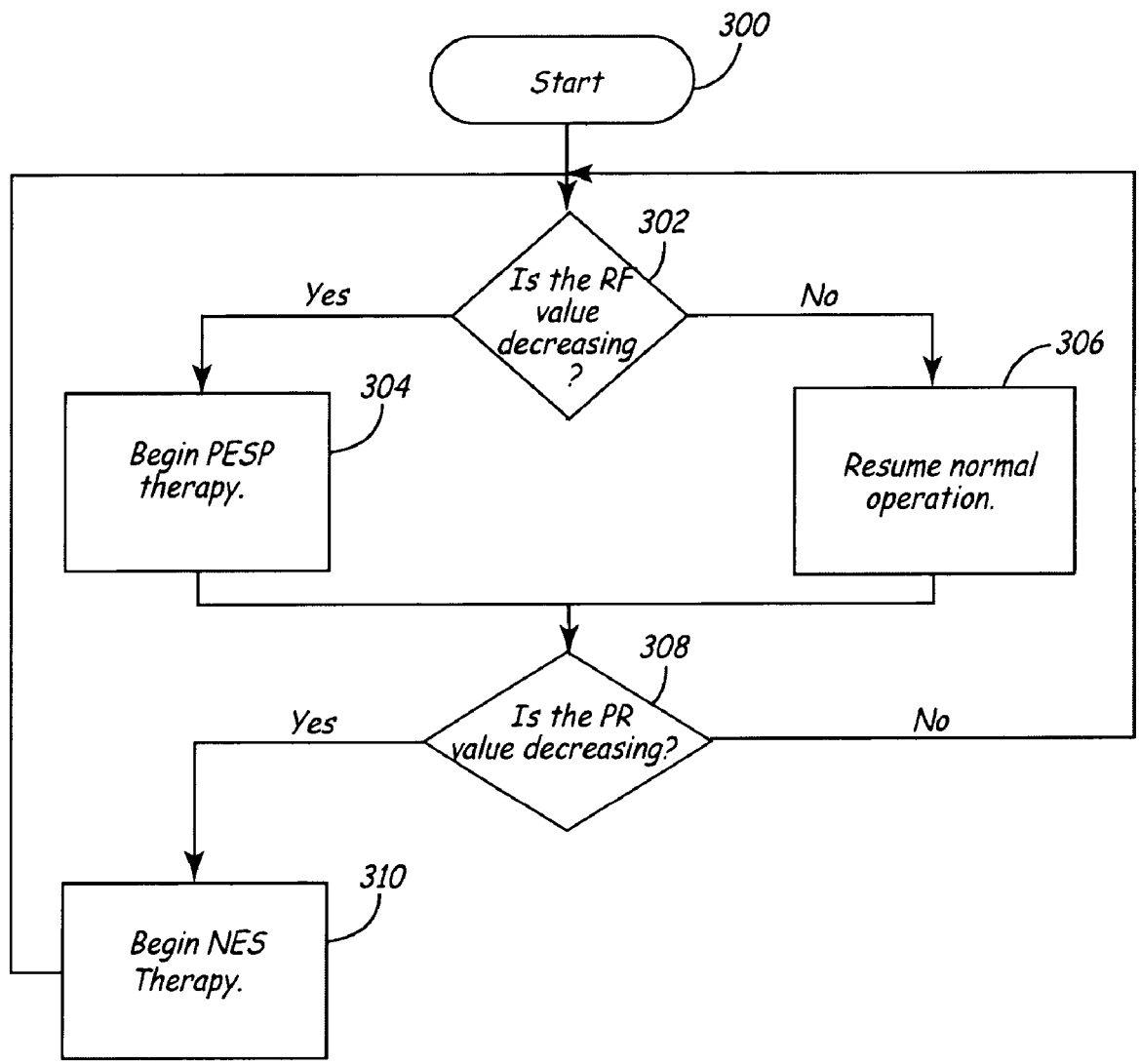
FIG. 26 is a flowchart diagram showing a method of combination PESP/NES pacing based upon recirculation fraction or potentiation ratio in an embodiment of the present invention.

With reference to FIG. 26, a flowchart diagram shows a method of combination PESP/NES pacing based upon using recirculation fraction and/or potentiation ratio physiologic feedback mechanism in an embodiment of the present invention. Another possible embodiment for determining which therapy should be applied and how it could be controlled includes the recirculation fraction (RF) or potentiation ratio (PR) derived from RV or LV pressure signals. A discussion of calculating RF and PR indices can be found in U.S. Patent Publication 2005/0075675A1 titled Method and apparatus for optimization and assessment of response to extra-systolic stimulation (ESS) therapy herein incorporated by reference in it's entirety. These measures have been shown to represent independent indices of calcium handling, with RF indicating an increased intracellular calcium concentration resulting in potentiation of contraction and the PR representing the speed with which the SR sequesters (takes up) calcium. For example, a fast decaying RF (approximately 0.2-0.4) implies quick dissipation of the extra calcium brought into the SR. Therefore, PESP may be necessary. A small PR (approximately 1.1-1.2) may indicate that not enough calcium is available to load the SR with PESP and that NES pacing will be required to bring additional calcium into the cell. In addition to the current state of these indices controlling which modes should be turned on and off, the response of the PR and/or RF to termination or initiation of the various therapies may be useful. For example, if adequate calcium is present within the cell, the initiation of NES (which brings additional calcium into the cell) will not change the RF or PR. If the intracellular calcium concentration is low, NES would result in an increased PR. The titration of these therapies could be handled by an algorithm discussed in a commonly owned patent application titled METHOD AND APPARATUS FOR OPTIMIZATION AND ASSESSMENT OF RESPONSE TO EXTRA-SYSTOLIC STIMULATION (ESS) THERAPY, filed on Oct. 7, 2003, assigned application Ser. No. 10/680,494 herein incorporated by reference in its entirety.

Upon initial programming at state 300, IMD 100 will begin normal operation. IMD 100 can determine if the RF value is decreasing at state 302 and if so can initiate a PESP therapy at state 304. If the RF value is maintaining a stable value at a predetermined value, IMD 100 can resume normal operation at state 306. IMD 100 can also determine if the PR value is decreasing at state 308 and if so, IMD 100 can initiate NES therapy at state 310. If the PR value is not decreasing and at a stable predetermined value, then IMD 100 once again inquires into the RF value. This routine is continuously run through to ensure efficient calcium handling by the myocardial cells.

Figure 27:
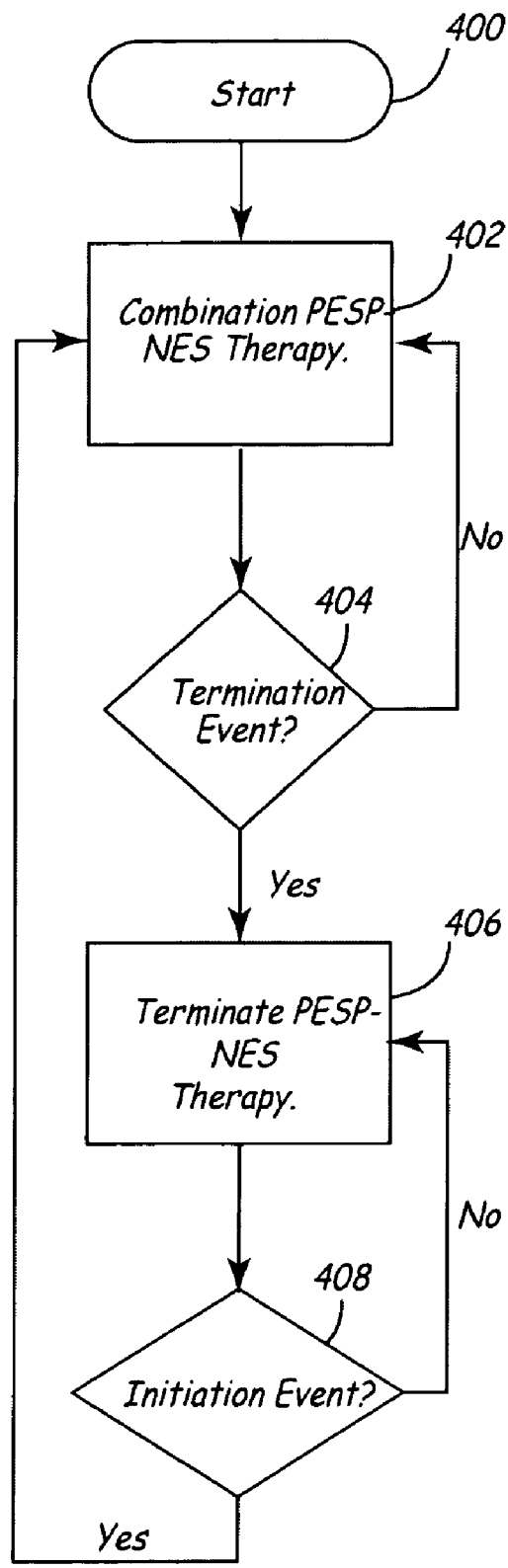
FIG. 27 is a flowchart diagram showing a method of initiation and termination of combination PESP/NES pacing in an embodiment of the present invention.

With reference to FIG. 27, a flowchart diagram showing a method of initiation and termination of combination PESP/NES pacing in an embodiment of the present invention is shown. There are several triggers, which could be used to initiate and terminate combination PESP, and NES pacing. Therapy can be initiated upon detection of atrial fibrillation (AF) and be terminated upon AF termination, to boost ventricular performance in the absence of atrial contribution to filling. It can be terminated upon the detection of sleep when the therapy is not necessarily needed thus saving battery energy and then initiated upon detection that the patient has awakened. It can also be initiated when sleep apnea is detected and good blood flow is desired and terminated when the apnea has passed. The therapy could also be terminated for a time period following an arrhythmia. Another application for combined PESP-NES therapy could be in the post resuscitation state following a defibrillation or cardioversion shock. In these instances it may be beneficial to "prime the cells" with calcium via NES before initiating PESP in order to more efficiently load the SR. A discussion of this application is discussed in commonly owned patent application titled METHOD AND APPARATUS FOR CARDIAC RESUSCITATION, filed on Sep. 22, 2003, assigned application Ser. No. 10/646,641 herein incorporated by reference in its entirety. It is fully contemplated that therapies could be initiated by the patient or caregiver upon anticipated exercise or with symptoms (e.g. shortness of breath).

Upon initial programming at state 400, IMD 100 will begin normal operation. At state 402, IMD 100 is operating in a normal combination PESP/NES therapy mode. If a termination event, such as those mentioned above, is detected at state 404, the PESP/NES therapy can be terminated at state 406. Then, if an initiation event, such as those discussed above is detected at state 408, the combination PESP/NES therapy can be initiated or reinitiated at state 402.

Thus, embodiments of the SYSTEM FOR ENHANCED CARDIAC FUNCTION WITH COMBINED PESP/NES are disclosed. One skilled in the art will appreciate that embodiments of the invention can be practiced with embodiments other than those disclosed. The disclosed embodiments are presented for purposes of illustration and not limitation, and embodiments of the invention are limited only by the claims that follow.

The invention claimed is:

1. A method of applying stimulation pulse therapy to excitable tissue, comprising:
   delivering a post extrasystolic potentiation (PESP) stimulation therapy to the excitable tissue for a cardiac cycle;
   delivering a non-excitatory stimulation (NES) stimulation therapy to the excitable tissue during certaincardiac cycles wherein the NES stimulation therapy is delivered on N of M cardiac cycles; and
   determining physiologic demand of the patient based on at least one physiologic measurement
   wherein N is variable and is based on the determined physiologic demand.

2. The method of claim 1, wherein N is decreased as the physiologic demand increases.

3. The method of claim 1, wherein N is increased as the physiologic demand decreases.

4. The method of claim 1, wherein PESP and NES stimulation occur in separate locations on the heart.

5. A method of applying stimulation pulse therapy to excitable tissue, comprising:
   delivering a PESP stimulation therapyto the excitable tissue for a cardiac cycle;
   delivering a NES stimulation therapy to the excitable tissue during certain cardiac cycles;
   determining physiologic demand being placed on a heart based on at least one physiologic measurement, and ceasing the delivery of the NES and PESP stimulation therapy when physiologic demand returns to a base level.

6. A method of applying stimulation pulse therapy to excitable tissue, comprising:
   delivering a PESP stimulation therapy to the excitable tissue for a cardiac cycle;
   delivering a NES stimulation therapy to the excitable tissue during certain cardiac cycles;
   determining physiologic demand being placed on a heart based on at least one physiologic measurement, and modulating the ratio of the number of cardiac cycles in which the NES stimulation therapy is delivered to the number of cardiac cycles in which the PESP stimulation therapy is delivered based on physiologic demand.

* * * * *

UNITED STATES PATENT AND TRADEMARK OFFICE
CERTIFICATE OF CORRECTION

PATENT NO. : 7,289,850 B2  Page 1 of 1
APPLICATION NO. : 11/116941
DATED : October 30, 2007
INVENTOR(S) : John Burnes et al.

It is certified that error appears in the above-identified patent and that said Letters Patent is hereby corrected as shown below:

On the Title Page, Item (73)
Assignee, delete "Medtronics, Inc." and insert in place there of --Medtronic, Inc.--.
Col. 34, line 27, delete "therapyto" and insert in place there of --therapy to--.

Signed and Sealed this

Sixth Day of January, 2009

JON W. DUDAS
*Director of the United States Patent and Trademark Office*